US011781163B2

(12) United States Patent
Chou et al.

(10) Patent No.: US 11,781,163 B2
(45) Date of Patent: Oct. 10, 2023

(54) REDUCING THE ACCUMULATION OF IMINES/ENAMINES FOR THE PRODUCTION OF AMINO ACIDS OR AMINO ACID-DERIVED PRODUCTS

(71) Applicants: CATHAY BIOTECH INC., Shanghai (CN); CIBT AMERICA INC., Newark, DE (US)

(72) Inventors: Howard Chou, Shanghai (CN); Ling Chen, Shanghai (CN); Xiucai Liu, Shanghai (CN)

(73) Assignees: CATHAY BIOTECH INC., Shanghai (CN); CIBT AMERICA INC., Newark, DE (US)

( * ) Notice: Subject to any disclaimer, the term of this patent is extended or adjusted under 35 U.S.C. 154(b) by 174 days.

(21) Appl. No.: 16/768,336

(22) PCT Filed: Nov. 29, 2017

(86) PCT No.: PCT/CN2017/113505
§ 371 (c)(1),
(2) Date: May 29, 2020

(87) PCT Pub. No.: WO2019/104518
PCT Pub. Date: Jun. 6, 2019

(65) Prior Publication Data
US 2021/0164003 A1    Jun. 3, 2021

(51) Int. Cl.
*C12P 13/08* (2006.01)
*C12N 9/12* (2006.01)
*C12N 9/78* (2006.01)
*C12N 9/88* (2006.01)
*C12P 13/00* (2006.01)

(52) U.S. Cl.
CPC .......... *C12P 13/08* (2013.01); *C12N 9/1217* (2013.01); *C12N 9/78* (2013.01); *C12N 9/88* (2013.01); *C12P 13/001* (2013.01); *C12Y 207/02004* (2013.01); *C12Y 305/99* (2013.01); *C12Y 401/0102* (2013.01); *C12Y 401/01018* (2013.01); *C12Y 402/01* (2013.01)

(58) Field of Classification Search
None
See application file for complete search history.

(56) References Cited

U.S. PATENT DOCUMENTS

2021/0164003 A1*  6/2021  Chou ................... C12P 13/08

FOREIGN PATENT DOCUMENTS

| CN | 101240258 A    | 8/2008 |
| EP | 2298880 A1     | 3/2011 |
| WO | 2016054792 A1  | 4/2016 |
| WO | 2017079872 A1  | 5/2017 |

OTHER PUBLICATIONS

Burland et al. (Nucleic Acid Research, vol. 13, 2105-2119, 1995).*
Extended European Search Report issued in corresponding European Application No. EP 17 93 3454, dated Jun. 7, 2021, 8 pages.
Zhi-Gang Qian et al: "Metabolic engineering of *Escherichia coli* for the production of cadaverine: A five carbon diamine", Biotechnology and Bioengineering, vol. 108, No. 1, Jan. 30, 2011, pp. 93-103. —.
International Search Report and Written Opinion issued in corresponding Application No. PCT/CN2017/113505, dated Aug. 30, 2018, 13 pags.
"GenBank Accession No. EOQ07422.1" GenBank DataBase, May 16, 2013 (May 16, 2013).
Lambrecht, J.A.et al. "RidA proteins prevent metabolic damage inflicted by PLP-dependent dehydratases in all domains of life" Mbio, vol. 4, No. 1, Feb. 28, 2013, 8 pages.

* cited by examiner

*Primary Examiner* — Hope A Robinson
(74) *Attorney, Agent, or Firm* — ROTHWELL, FIGG, ERNST & MANBECK, P.C.

(57) ABSTRACT

Provided microorganisms genetically modified to overexpress an imine/enamine deaminase to enhance the production of lysine and lysine derivatives by the microorganism. Also provided a method of generating such microorganism, and methods of producing lysine and lysine derivatives using the genetically modified microorganisms.

14 Claims, 2 Drawing Sheets
Specification includes a Sequence Listing.

Figure 1

```
CLUSTAL O(1.2.4) multiple sequence alignment

1PF5:A      MVERTAVFPAGRHSLYAEHRYSAAIRSGDLLFVSGQVGSRED--GTPEPDFQQQVRLAFD
5HP7:A      -----GPHMSTEKAPAALGPYSQAIKANNLVFLSGVLGLIPETGKFVSESVEDQTEQVLK
2UYN:A      ----MKKIIETQRAPGAIGPYVQGVDLGSMVFTSGQIPVCPQTGEIPA-DVQDQARLSLE
1QU9:A      ----MSKTIATENAPAAIGPYVQGVDLGNMIITSGQIPVNPKTGEVPA-DVAAQARQSLD
                 ..:    *     *  .:  ..:::  **  :    .       ..  *..  :.

1PF5:A      NLHATLAAAGCTFDDIIDVTSFHTDPENQFEDIMTVKNEIFSA---PPYPNWTAVGVTWLA
5HP7:A      NMGEILKASGADYSSVVKTTIMLADLA-DFKTVNEIYAKYFPA---PSPARSTYQVAALP
2UYN:A      NVKAIVVAAGLSVGDIIKMTVFITDLN-DFATINEVYKQFFDEHQATYPTRSCVQVARLP
1QU9:A      NVKAIVEAAGLKVGDIVKTTVFVKDLN-DFATVNATYEAFFTEHNATFPARSCVEVARLP
             *:    :  *:*    ..::. *  :   :*    :           *      * :  *:*  *

1PF5:A      -GFDFEIKVIARIPEQ
5HP7:A      LNAKIEIECIATL---
2UYN:A      KDVKLEIEAIAVRSA-
1QU9:A      KDVKIEIEAIAVRR--
              . .:**: **
```

Figure 2

```
CLUSTAL O(1.2.4) multiple sequence alignment

EcYjgH      MVERTAVFPAGRHSLYAEHRYSAAIRSGDLLFVSGQVGSRED--GTPEPDFQQQVRLAFD
EcYoaB      ----MTIVRI--DA----EARW------SDVVIHNNTLYYTG-VPENLDADAFEQTANTLA
EcRutC      MP-KSVIIPA--GSSAPLAPFVPGTLADGVVYVSGTLAFDQHNNVLFADDPKAQTRHVLE
EcTdcF      -M-KKIIETQ--RAPGAIGPYVQGVDLGSMVFTSGQIPVCPQTGEI-PADVQDQARLSLE
EcRidA      -M-SKTIATE--NAPAAIGPYVQGVDLGNMIITSGQIPVNPKTGEV-PADVAAQARQSLD
                 :         :         :      ..::  .. :          *    *.   :

EcYjgH      NLHATLAAAGCTFDDIIDVTSFHTDPENQFEDIMTVKNEIFSAP--PYPNWTAVGVTWL-
EcYoaB      QIDAVLEKQGSNKSSILDATIFLADKND-FAAMNKAWDAWVVAG--HAPVRCTVQAGLMN
EcRutC      TIRKVIETAGGTMADVTFNSIFITDWKN-YAAINEIYAEFFPGD---KPARFCIQCGLVK
EcTdcF      NVKAIVVAAGLSVGDIIKMTVFITDLND-FATINEVYKQFFDEHQATYPTRSCVQVARLP
EcRidA      NVKAIVEAAGLKVGDIVKTTVFVKDLND-FATVNATYEAFFTEHNATFPARSCVEVARLP
             :    :   *   .  .:    :  *   * ::  :  :        .      *     :   :

EcYjgH      AGFDFEIKVIARIPEQ
EcYoaB      PKYKVEIKIVAAV*--
EcRutC      PDALVEIATIAHIAK-
EcTdcF      KDVKLEIEAIAVRSA-
EcRidA      KDVKIEIEAIAVRR--
                  .**  :*
```

REDUCING THE ACCUMULATION OF IMINES/ENAMINES FOR THE PRODUCTION OF AMINO ACIDS OR AMINO ACID-DERIVED PRODUCTS

CROSS REFERENCE TO RELATED APPLICATION

This application is a 35 U.S.C. 371 National Phase Entry Application from PCT/CN2017/113505, filed Nov. 29, 2017, the disclosure of which is incorporated herein in its entirety by reference.

BACKGROUND OF THE INVENTION

The overproduction of amino acids, such as lysine, and amino acid-derived products, such as cadaverine, often requires the remodeling of the host cell's metabolism in order to increase the flux of the carbon and nitrogen containing compounds towards the desired products. However, modifying the flux of metabolic pathways can lead to the accumulation of intermediates that do not normally accumulate inside the cell. Such metabolic intermediates may be either the final product of an enzymatic reaction or an intermediate of an enzymatic reaction that leaks out of the catalytic site of the enzyme. The metabolic intermediate that accumulates may also be toxic to the cell, or induce the activity of other pathways that transform the intermediate into a compound that is toxic to the cell (Danchin, *Microbial Biotechnology* 10:57-72, 2017).

Imine/enamine intermediates often form during transamination, racemization, or deamination reactions that lead to the formation of reactive amino acid derivatives (e.g., aminoacrylate or iminopropionate). Imine/enamine formation sometimes involves the cofactor pyridoxal phosphate (PLP). Reactive imines/enamines are known to cause cellular damage and can accumulate inside the cell during the overproduction of amino acids, such as lysine, and amino acid-derived products, such as cadaverine. For example, the overproduction of lysine or cadaverine in *Escherichia coli* can involve the remodeling of the host metabolism in such a way that leads to the production of imine/enamine compounds.

The overproduction of lysine or cadaverine involves the overexpression of genes encoding one or more of the following proteins: dihydrodipicolinate synthase (DHDPS, EC 4.2.1.52), diaminopimelate dehydrogenase (DAPDH, EC 1.4.1.16), and diaminopimelate decarboxylase (DAPDC, EC 4.1.1.20) (Anastassiadis, Recent Patents on Biotechnology 1: 11-24, 2007). DHDPS catalyzes the condensation of pyruvate and aspartate semialdehyde to form 4-hydroxy-2,3,4,5-tetrahydro-L,L-dipicolinic acid, which involves the formation of an imine intermediate (Dobson et al., *Protein Science* 17:2080-2090, 2008). DAPDH catalyzes the reductive amination of L-2-amino-6-ketopimelate, which creates an imine intermediate that is reduced by NADPH to produce meso-DAP (Scapin et al., *Biochemistry* 37: 3278-3285, 1998). DAPDC is a PLP-dependent enzyme that catalyzes the decarboxylation of meso-DAP to lysine. Certain DAPDCs form an aldimine in the presence of PLP (Hu et al., *J. Biol. Chem.* 283: 21284-21293, 2008).

Lysine, threonine, and methionine share the same upstream metabolic pathway, since all three amino acids are derived from aspartate. The conversion of aspartate to the precursors of lysine, threonine, or methionine is catalyzed by three different aspartate kinases, one for each amino acid (LysC, MetL, ThrA). However, increasing the flux through aspartate biosynthesis in order to increase either lysine or cadaverine production will also increase threonine production, since they share a common precursor. The accumulation of threonine in the cell can trigger the activity of threonine dehydratase (EC 4.3.1.19), which is the first enzyme involved in the catabolism of threonine to isoleucine. Threonine dehydratase is a PLP-dependent enzyme that catalyzes the dehydration of threonine to aminocrotonoate, an enamine intermediate. Aminocrotonoate can tautomerize to iminobutyrate, an imine intermediate. Therefore, the accumulation of threonine in the cell can increase the accumulation of these toxic enamine/imine intermediates inside the cell.

In certain cases, the flux through the threonine biosynthesis pathway is reduced or eliminated in order to increase the flux of carbon- and nitrogen-containing compounds going towards lysine and cadaverine biosynthesis. However, threonine needs to be added to the medium in order to ensure that the intracellular concentration of threonine is sufficient for cell growth. The addition of external threonine may lead to the addition of sufficient threonine that the amino acid accumulates inside the cell, in which case, the accumulation of aminocrotonoate and iminobutyrate can result as described above.

The conversion of lysine to cadaverine involves the PLP-dependent enzyme lysine decarboxylase. Therefore, overproduction of cadaverine involves increasing the intracellular concentration of PLP, which can be accomplished by adding PLP to the medium or overexpressing genes involved in the synthesis of PLP (e.g., pdxST). As described above, some of the reactions that lead to the accumulation of imine/enamine are PLP-catalyzed reactions. Therefore, an increase in the intracellular concentration of PLP increases the probability for imine/enamine to form and accumulate inside the cell.

It was discovered that *Salmonella enterica* produces a protein RidA (YjgF) that has imine/enamine deaminase activity, allowing it to catalyze the release of ammonia and the production of a more stable and less toxic intermediate from imine/enamine compounds (Lambrecht et al., *J. Biol. Chem.* 287: 3454-3461, 2012). RidA protects *S. enterica* from the harmful imine/enamine molecules formed by the activity of the PLP-dependent threonine dehydratase (IlvA) by catalyzing the removal of ammonia from the intermediate enamine/imine compounds to form the nontoxic 2-ketobutyrate. The activity of RidA was also shown to protect cells from 2-aminoacrylate, an enamine formed during serine catabolism (Lambrecht et al., *mBio* 4: 1-8, 2013). The accumulation of imines/enamines also inactivates the PLP-catalyzed enzymes in the cell, so the removal of imines/enamines is important.

BRIEF SUMMARY OF ASPECTS OF THE INVENTION

Provided herein are host cells genetically modified to enhance removal of imine and enamine compounds and thus increase, relative to host cells of the same strain that do not have the genetic modification to enhance imine and enamine removal, the production of an amino acid or amino acid derivate for which imine and/or enamine is an intermediate. Also provided herein are methods of generating such host cells; and methods of using the host cells to produce increased yields of an amino acid or amino acid derivative, such as lysine or cadaverine.

Thus, in one aspect, provided herein is a method of engineering a host cell to increase production of an amino acid or an amino acid derivative, e.g., lysine or cadaverine, the method comprising introducing a polynucleotide, e.g., heterologous polynucleotide, comprising a nucleic acid that encodes an imine/enamine deaminase polypeptide into the host cell, wherein the host cell has at least one additional genetic modification that increases production of the amino acid or the amino acid derivative compared to wildtype host cell; culturing the host cell under conditions in which the imine/enamine deaminase polypeptide is expressed, and selecting a host cell that produces an increased amount of an amino acid or amino acid derivative, e.g., lysine or cadaverine, relative to a counterpart host cell of the same strain that has not been modified to express the polynucleotide encoding the imine/enamine deaminase polypeptide. In some embodiments, the imine/enamine deaminase polypeptide is a YoaB polypeptide. In some embodiments, the imine/enamine deaminase polypeptide has at least 70% amino acid sequence identity to SEQ ID NO:10. In some embodiments, the imine/enamine deaminase polypeptide has at least 80% identity to the amino acid sequence of SEQ ID NO:10. In some embodiments, the imine/enamine deaminase polypeptide has at least 90% identity to the amino acid sequence of SEQ ID NO:10. In some embodiments, the imine/enamine deaminase polypeptide has at least 95% identity to the amino acid sequence of SEQ ID NO:10. In some embodiments, the imine/enamine polypeptide comprises the amino acid sequence of SEQ ID NO:10. In some embodiments, the imine/enamine deaminase polypeptide is a YjgH polypeptide. In some embodiments, the imine/enamine deaminase polypeptide has at least 70% amino acid sequence identity to SEQ ID NO:12. In some embodiments, the imine/enamine deaminase polypeptide has at least 80% identity to the amino acid sequence of SEQ ID NO:12. In some embodiments, the imine/enamine deaminase polypeptide has at least 90% identity to the amino acid sequence of SEQ ID NO:12. In some embodiments, the imine/enamine deaminase polypeptide has at least 95% identity to the amino acid sequence of SEQ ID NO:12. In some embodiments, the imine/enamine deaminase polypeptide comprises the amino acid sequence of SEQ ID NO:12. In some embodiments, the polynucleotide is contained in an expression vector introduced into the cell, wherein the expression vector comprises the polynucleotide operably linked to a promoter. In other embodiments, the polynucleotide introduced into the host cell is integrated into the host chromosome. In some embodiments, the genetically modified host cell is additionally modified to overexpress an exogenous lysine decarboxylase; and/or one or more exogenous lysine biosynthesis polypeptides. In some embodiments, the genetically modified host cell additionally overexpresses an exogenous LysC, DapA, LysA, Asd, DapB, or AspC polypeptide. In some embodiments, the genetically modified host cell is additionally modified to overexpress exogenous CadA, LysC, DapA, LysA, Asd, DapB, and AspC polypeptides. In some embodiments, the genetically modified host cell is of the genus *Escherichia*, e.g., *Escherichia coli*; *Hafnia*, e.g., *Hafnia alvei*; or *Corynebacterium*, e.g., *Corynebacterium glutamicum*.

In another aspect, provided herein is a genetically modified host cell produced according to a method of the preceding paragraph.

In a further aspect, provided herein is a genetically modified host cell comprising a polynucleotide, e.g., a heterologous polynucleotide, comprising a nucleic acid encoding an imine/enamine deaminase polypeptide that increases the amount of an amino acid, e.g., lysine, or amino acid derivative, e.g., cadaverine, compared to a counterpart host cell that has not been modified to express the polynucleotide encoding the imine/enamine polypeptide; and has at least one additional genetic modification that increases production of the amino acid or the amino acid derivative compared to wildtype host cells. In some embodiments, the imine/enamine deaminase polypeptide is a YoaB polypeptide. In some embodiments, the imine/enamine deaminase polypeptide has at least 70% amino acid sequence identity to SEQ ID NO:10. In some embodiments, the imine/enamine deaminase polypeptide has at least 80% identity to the amino acid sequence of SEQ ID NO:10. In some embodiments, the imine/enamine deaminase polypeptide has at least 90% identity to the amino acid sequence of SEQ ID NO:10. In some embodiments, the imine/enamine deaminase polypeptide has at least 95% identity to the amino acid sequence of SEQ ID NO:10. In some embodiments, the imine/enamine deaminase polypeptide is a YjgH polypeptide. In some embodiments, the imine/enamine deaminase polypeptide has at least 70% amino acid sequence identity to SEQ ID NO:12. In some embodiments, the imine/enamine deaminase polypeptide has at least 80% identity to the amino acid sequence of SEQ ID NO:12. In some embodiments, the imine/enamine deaminase polypeptide has at least 90% identity to the amino acid sequence of SEQ ID NO:12. In some embodiments, the imine/enamine deaminase polypeptide has at least 95% identity to the amino acid sequence of SEQ ID NO:12. In some embodiments, the imine/enamine deaminase polypeptide comprises the amino acid sequence of SEQ ID NO:10 or SEQ ID NO:12. In some embodiments, the polynucleotide is contained in an expression vector introduced into the cell, wherein the expression vector comprises the polynucleotide operably linked to a promoter. In other embodiments, the polynucleotide introduced into the host cell is integrated into the host chromosome. In some embodiments, the genetically modified host cell additionally overexpresses a lysine decarboxylase; and/or one or more lysine biosynthesis polypeptides. In some embodiments, the genetically modified host cell is of the genus *Escherichia*, e.g., *Escherichia coli*; *Hafnia*, e.g., *Hafnia alvei*; or *Corynebacterium*, e.g., *Corynebacterium glutamicum*. In some embodiments, the genetically modified host cell additionally overexpresses a LysC, DapA, LysA, Asd, DapB, or AspC polypeptide. In some embodiments, the genetically modified host cell additionally overexpresses a CadA, LysC, DapA, LysA, Asd, DapB, and AspC polypeptide.

In a further aspect, provided herein is a method of producing an amino acid or an amino acid derivative, e.g., lysine or cadaverine, the method comprising culturing a host cell as set forth in the two preceding paragraphs under conditions in which the imine/enamine deaminase polypeptide is expressed. In some embodiments, the method further comprises isolating the amino acid or amino acid derivative, e.g., lysine or cadaverine.

BRIEF DESCRIPTION OF THE DRAWINGS

FIG. 1 provides an illustrative alignment of RidA homolog protein sequences (identified by PDB accession numbers). 1PF5 corresponds to SEQ ID NO: 12; 5HP7 corresponds to SEQ ID NO: 82; 2UYN corresponds to SEQ ID NO: 8; and 1QU9 corresponds to SEQ ID NO: 4.

FIG. 2 provides an illustrative alignment of *E. coli* RidA and paralog protein sequences. Positions corresponding to E120, C107, V18, K73, and E122 of RidA are underlined. Amino acids at positions D76 and K123 of YjgH, corresponding to positions K73 and E122 of RidA, respectively)

are conserved in the YjgH and YoaB sequences and are shown in bold, enlarged font. EcYjgH corresponds to SEQ ID NO: 12; EcYoaB corresponds to SEQ ID NO: 10; EcRutC corresponds to SEQ ID NO: 6; EcTdcF corresponds to SEQ ID NO: 8; and EcRidA corresponds to SEQ ID NO: 4.

DETAILED DESCRIPTION OF ASPECTS OF THE INVENTION

Terminology

As used in the context of the present disclosure, an "imine/enamine deaminase polypeptide" refers to an enzyme that decreases imine/enamine levels in a host cells. Such a polypeptide catalyzes the release of ammonia from imine/enamine. A polypeptide that decreases imine/enamine levels in accordance with the disclosure typically decreases levels by at least 10%, at least 15%, at least 20%, at least 25%, at least 30%, at least 35%, at least 40%, at least 45%, or at least 50%, or greater, when produced by a host cell genetically modified to overexpress the imine/enamine deaminase polypeptide compared to a wildtype counterpart host cell that has not been genetically modified to overexpress the imine/enamine deaminase polypeptide.

The term "imine/enamine deaminase polypeptide" encompasses biologically active variants, alleles, mutants, and interspecies homologs to the specific polypeptides described herein. A nucleic acid that encodes an imine/enamine deaminase polypeptide refers to a gene, pre-mRNA, mRNA, and the like, including nucleic acids encoding variants, alleles, mutants, and interspecies homologs of the particular amino acid sequences described herein.

The terms "increased expression" and "overexpression" of an imine/enamine deaminase polypeptide are used interchangeably herein to refer to an increase in the amount of imine/enamine deaminase polypeptide in a genetically modified cell, e.g., a cell into which an expression construct encoding imine/enamine deaminase polypeptide has been introduced, compared to the amount of imine/enamine deaminase polypeptide in a counterpart cell that does not have the genetic modification, i.e., a cell of the same strain without the modification. An increased level of expression for purposes of this application is at least 5%, or at least 10%, 20%, 30%, 40%, 50%, 60%, 70%, 80%, 90%, 100%, or greater, compared to the counterpart unmodified cell. The unmodified cell need not express the imine/enamine deaminase. Thus, the term "overexpression" also includes embodiments in which an imine/enamine deaminase polypeptide is expressed in a host cell that does not natively express the imine/enamine deaminase polypeptide. Increased expression of an imine/enamine deaminase polypeptide can be assessed by any number of assays, including, but not limited to, measuring the level of RNA transcribed from the imine/enamine deaminase gene, the level of imine/enamine deaminase polypeptide, and/or the level of imine/enamine deaminase polypeptide activity.

The term "enhanced" in the context of the production of an amino acid, e.g., lysine, or an amino acid derivative, e.g., a lysine derivative, such as cadaverine, as used herein refers to an increase in the production of amino acid, e.g., lysine, or the derivative by a genetically modified host cell in comparison to a control counterpart cell, such as a cell of the wildtype strain or a cell of the same strain that does not have the genetic modification to increase production of the amino acid or amino acid derivative. Production of the amino acid or its derivative is enhanced by at least 5%, typically at least 10%, 20%, 30%, 40%, 50%, 60%, 70%, 80%, 90%, 100%, or greater compared to the control cell.

The terms "numbered with reference to", or "corresponding to," or "determined with reference to" when used in the context of the numbering of a given amino acid or polynucleotide sequence, refers to the numbering of the residues of a specified reference sequence when the given amino acid or polynucleotide sequence is compared to the reference sequence. For example, a residue in a YoaB polypeptide variant or homolog "corresponds to" an amino acid at a position in SEQ ID NO:10 when the residue aligns with the amino acid in a comparison of SEQ ID NO:10 and the homolog or variant in a maximal alignment. Similarly, a residue in a YjgH polypeptide variant "corresponds to" an amino acid at a position in SEQ ID NO:12 when the residue aligns with the amino acid in a comparison of SEQ ID NO:12 and the homolog or variant in a maximal alignment.

The terms "polynucleotide" and "nucleic acid" are used interchangeably and refer to a single or double-stranded polymer of deoxyribonucleotide or ribonucleotide bases read from the 5' to the 3' end. A nucleic acid as used in the present invention will generally contain phosphodiester bonds, although in some cases, nucleic acid analogs may be used that may have alternate backbones, comprising, e.g., phosphoramidate, phosphorothioate, phosphorodithioate, or O-methylphosphoroamidite linkages (see Eckstein, Oligonucleotides and Analogues: A Practical Approach, Oxford University Press); positive backbones; non-ionic backbones, and non-ribose backbones. Nucleic acids or polynucleotides may also include modified nucleotides that permit correct read-through by a polymerase. "Polynucleotide sequence" or "nucleic acid sequence" includes both the sense and antisense strands of a nucleic acid as either individual single strands or in a duplex. As will be appreciated by those in the art, the depiction of a single strand also defines the sequence of the complementary strand; thus the sequences described herein also provide the complement of the sequence. Unless otherwise indicated, a particular nucleic acid sequence also implicitly encompasses variants thereof (e.g., degenerate codon substitutions) and complementary sequences, as well as the sequence explicitly indicated. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc. Nucleic acid sequences are presented in the 5' to 3' direction unless otherwise specified.

The term "substantially identical," used in the context of two nucleic acids or polypeptides, refers to a sequence that has at least 40%, 45%, or 50% sequence identity with a reference sequence. Percent identity can be any integer from 50% to 100%. Some embodiments include at least: 50%, 55%, 60%, 65%, 70%, 75%, 80%, 85%, 90%, 91%, 92%, 93%, 94%, 95%, 96%, 97%, 98%, or 99%, compared to a reference sequence using the programs described herein; preferably BLAST using standard parameters, as described below.

Two nucleic acid sequences or polypeptide sequences are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

An algorithm that may be used to determine whether an imine/enamine deaminase polypeptide has sequence identity to SEQ ID NO:10 or 12, or another polypeptide reference sequence, is the BLAST algorithm, which is described in Altschul et al., 1990, J. Mol. Biol. 215:403-410, which is incorporated herein by reference. Software for performing BLAST analyses is publicly available through the National Center for Biotechnology Information (on the worldwide web at ncbi.nlm.nih.gov/). For amino acid sequences, the BLASTP program uses as defaults a word size (W) of 3, an expectation (E) of 10, and the BLOSUM62 scoring matrix (see Henikoff & Henikoff, 1989, Proc. Natl. Acad. Sci. USA 89:10915). Other programs that may be used include the Needleman-Wunsch procedure, J. Mol. Biol. 48: 443-453 (1970), using BLOSUM62, a Gap start penalty of 7 and gap extend penalty of 1; and gapped BLAST 2.0 (see Altschul, et al. 1997, Nucleic Acids Res., 25:3389-3402) both A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

Nucleic acid or protein sequences that are substantially identical to a reference sequence include "conservatively modified variants." With respect to particular nucleic acid sequences, conservatively modified variants refer to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, in a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Examples of amino acid groups defined in this manner can include: a "charged/polar group" including Glu (Glutamic acid or E), Asp (Aspartic acid or D), Asn (Asparagine or N), Gln (Glutamine or Q), Lys (Lysine or K), Arg (Arginine or R) and His (Histidine or H); an "aromatic or cyclic group" including Pro (Proline or P), Phe (Phenylalanine or F), Tyr (Tyrosine or Y) and Trp (Tryptophan or W); and an "aliphatic group" including Gly (Glycine or G), Ala (Alanine or A), Val (Valine or V), Leu (Leucine or L), Ile (Isoleucine or I), Met (Methionine or M), Ser (Serine or S), Thr (Threonine or T) and Cys (Cysteine or C). Within each group, subgroups can also be identified. For example, the group of charged/polar amino acids can be sub-divided into sub-groups including: the "positively-charged sub-group" comprising Lys, Arg and His; the "negatively-charged sub-group" comprising Glu and Asp; and the "polar sub-group" comprising Asn and Gln. In another example, the aromatic or cyclic group can be sub-divided into sub-groups including: the "nitrogen ring sub-group" comprising Pro, His and Trp; and the "phenyl sub-group" comprising Phe and Tyr. In another further example, the aliphatic group can be sub-divided into sub-groups including: the "large aliphatic non-polar sub-group" comprising Val, Leu and Ile; the "aliphatic slightly-polar sub-group" comprising Met, Ser, Thr and Cys; and the "small-residue sub-group" comprising Gly and Ala. Examples of conservative mutations include amino acid substitutions of amino acids within the sub-groups above, such as, but not limited to: Lys for Arg or vice versa, such that a positive charge can be maintained; Glu for Asp or vice versa, such that a negative charge can be maintained; Ser for Thr or vice versa, such that a free —OH can be maintained; and Gln for Asn or vice versa, such that a free —NH2 can be maintained. The following six groups each contain amino acids that further provide illustrative conservative substitutions for one another. 1) Ala, Ser, Thr; 2) Asp, Glu; 3) Asn, Gln; 4) Arg, Lys; 5) Ile, Leu, Met, Val; and 6) Phe, Try, and Trp (see, e.g., Creighton, Proteins (1984)).

The term "promoter," as used herein, refers to a polynucleotide sequence capable of driving transcription of a DNA sequence in a cell. Thus, promoters used in the polynucleotide constructs of the invention include cis- and trans-acting transcriptional control elements and regulatory sequences that are involved in regulating or modulating the timing and/or rate of transcription of a gene. For example, a promoter can be a cis-acting transcriptional control element, including an enhancer, a repressor binding sequence and the like. These cis-acting sequences typically interact with proteins or other biomolecules to carry out (turn on/off, regulate, modulate, etc.) gene transcription. Most often the core promoter sequences lie within 1-2 kb of the translation start site, more often within 1 kbp and often within 500 bp or 200 bp or fewer, of the translation start site. By convention, promoter sequences are usually provided as the sequence on the coding strand of the gene it controls. In the context of this application, a promoter is typically referred to by the name of the gene for which it naturally regulates expression. A promoter used in an expression construct of the invention is referred to by the name of the gene. Reference to a promoter by name includes a wild type, native promoter as well as variants of the promoter that retain the ability to induce expression. Reference to a promoter by name is not restricted to a particular species, but also encompasses a promoter from a corresponding gene in other species.

A "constitutive promoter" in the context of this invention refers to a promoter that is capable of initiating transcription under most conditions in a cell, e.g., in the absence of an inducing molecule. An "inducible promoter" initiates transcription in the presence of an inducer molecule.

As used herein, a polynucleotide is "heterologous" to an organism or a second polynucleotide sequence if it originates from a foreign species, or, if from the same species, is modified from its original form. For example, when a polynucleotide encoding a polypeptide sequence is said to be operably linked to a heterologous promoter, it means that the polynucleotide coding sequence encoding the polypeptide is derived from one species whereas the promoter sequence is derived from another, different species; or, if both are derived from the same species, the coding sequence is not naturally associated with the promoter (e.g., is a genetically engineered coding sequence, e.g., from a different gene in the same species, or an allele from a different species). Similarly, a polypeptide is "heterologous" to a host cell if the native wildtype host cell does not produce the polypeptide.

The term "exogenous" as used herein refers generally to a polynucleotide sequence or polypeptide that is introduced into a host cell by molecular biological techniques to produce a recombinant cell. Examples of "exogenous" polynucleotides include vectors, plasmids, and/or man-made nucleic acid constructs encoding a desired protein. An "exogenous" polypeptide expressed in the host cell may occur naturally in the wildtype host cell or may be heterologous to the host cell. The term also encompasses progeny of the original host cell that has been engineered to express the exogenous polynucleotide or polypeptide sequence, i.e., a host cell that expresses an "exogenous" polynucleotide may be the original genetically modified host cell or a progeny cell that comprises the genetic modification.

The term "endogenous" refers to naturally-occurring polynucleotide sequences or polypeptides that may be found in a given wild-type cell or organism. In this regard, it is also noted that even though an organism may comprise an endogenous copy of a given polynucleotide sequence or gene, the introduction of an expression construct or vector encoding that sequence, such as to over-express or otherwise regulate the expression of the encoded protein, represents an "exogenous" copy of that gene or polynucleotide sequence. Any of the pathways, genes, or enzymes described herein may utilize or rely on an "endogenous" sequence, which may be provided as one or more "exogenous" polynucleotide sequences, or both.

"Recombinant nucleic acid" or "recombinant polynucleotide" as used herein refers to a polymer of nucleic acids wherein at least one of the following is true: (a) the sequence of nucleic acids is foreign to (i.e., not naturally found in) a given host cell; (b) the sequence may be naturally found in a given host cell, but in an unnatural (e.g., greater than expected) amount; or (c) the sequence of nucleic acids comprises two or more subsequences that are not found in the same relationship to each other in nature. For example, regarding instance (c), a recombinant nucleic acid sequence will have two or more sequences from unrelated genes arranged to make a new functional nucleic acid.

The term "operably linked" refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a DNA or RNA sequence if it stimulates or modulates the transcription of the DNA or RNA sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The term "expression cassette" or "DNA construct" or "expression construct" refers to a nucleic acid construct that, when introduced into a host cell, results in transcription and/or translation of an RNA or polypeptide, respectively. In the case of expression of transgenes, one of skill will recognize that the inserted polynucleotide sequence need not be identical, but may be only substantially identical to a sequence of the gene from which it was derived. As explained herein, these substantially identical variants are specifically covered by reference to a specific nucleic acid sequence. One example of an expression cassette is a polynucleotide construct that comprises a polynucleotide sequence encoding a polypeptide for use in the invention operably linked to a promoter, e.g., its native promoter, where the expression cassette is introduced into a heterologous microorganism. In some embodiments, an expression cassette comprises a polynucleotide sequence encoding a polypeptide of the invention where the polynucleotide that is targeted to a position in the genome of a microorganism such that expression of the polynucleotide sequence is driven by a promoter that is present in the microorganism.

The term "host cell" as used in the context of this invention refers to a microorganism and includes an individual cell or cell culture that can be or has been a recipient of any recombinant vector(s) or isolated polynucleotide(s) of the invention. Host cells include progeny of a single host cell, and the progeny may not necessarily be completely identical (in morphology or in total DNA complement) to the original parent cell due to natural, accidental, or deliberate mutation and/or change. A host cell includes cells into which a recombinant vector or a polynucleotide of the invention has been introduced, including by transformation, transfection, and the like.

The term "isolated" refers to a material that is substantially or essentially free from components that normally accompany it in its native state. For example, an "isolated polynucleotide," as used herein, may refer to a polynucleotide that has been isolated from the sequences that flank it in its naturally-occurring or genomic state, e.g., a DNA fragment that has been removed from the sequences that are normally adjacent to the fragment, such as by cloning into a vector. A polynucleotide is considered to be isolated if, for example, it is cloned into a vector that is not a part of the natural environment, or if it is artificially introduced in the genome of a cell in a manner that differs from its naturally-occurring state. Alternatively, an "isolated peptide" or an "isolated polypeptide" and the like, as used herein, refers to a polypeptide molecule that is free of other components of the cell, i.e., it is not associated with in vivo substances.

Aspects of the Disclosure

The present disclosure is based, in part, on the discovery that increased expression of one or more imine/enamine deaminase polypeptides in a microorganism, such as a gram-negative bacterium, enhances amino acid, e.g., lysine, production and/or production of an amino acid derivative of lysine, such as cadaverine.

RidA is a member of the YjgF/YER057c/UK114 family that is conserved in all domains of life (pfam: PF01042). The members of this family are small proteins of about 15 kDa, and form homotrimers—a trimeric barrel-like quaternary structure. The family members have diverse phenotypes and do not have a clearly defined biological role like most other well-defined protein families with defined substrates and products (e.g., P450 mono-oxidase, DNA polymerase, or lysine decarboxylase). Recently, the crystal structure of RidA from *Arapidopsis thaliana* was published (PBD ID: 5HP7) (Lu et al., Scientific Reports 6: 30494, 2016). The crystal structures of other members of this family have also been published (PBD ID: 1QD9 *Bacillus subtilis* YabJ, 1X25 of *Sulfolobus tokodaii* YjgF member, 1QU9 of *E. coli* RidA, 2UYN of *E. coli* TdcF, 1ONI of human p14.5). Sequences of RidA homolog proteins (identified by PDB accession numbers) are shown in FIG. 1. The members of this family have several important residues involved in trimer formation and substrate binding. Five of these positions are indicated by underline in the 5HP7 amino acid sequence.

*Escherichia coli* also expresses a gene encoding RidA. *E. coli* RidA has been shown to be important in the synthesis of thiamine (Bazurto et al., mBio 7: 1-9, 2016), and can also function as a chaperone protein during oxidative stress (Muller et al., Nature Communications 5: 1-14, 2014). The overexpression of enzymes in order to increase metabolic flux towards the production of lysine is expected to produce metabolic burden and stress on the cell; therefore, it would be expected that the overexpression of RidA would help to remove toxic intermediates formed as a result of metabolic stress and increase lysine production. Surprisingly, it was discovered here that the overexpression of *E. coli* RidA did not increase the production of lysine.

However, *E. coli* also contains four paralogs of RidA, which are YjgH, TdcF, RutC, and YoaB. Surprisingly, it was observed that the overexpression of certain paralogs did lead to a change in lysine and cadaverine production. For example, the overexpression of the genes encoding YjgH and YoaB increased lysine and cadaverine production.

The crystal structure of *E. coli* YjgH has been solved (PDB ID: 1PF5). Crystal structure analysis of 1PF5 and 1QU9 using the Needleman-Wunsch algorithm and Blosum 62 matrix in UCSF Chimera shows that the two structures can be superimposed on top of each other with extremely high similarity.

An amino acid sequence alignment of *E. coli* RidA and its paralogs YjgH, YoaB, RutC, and TdcF are shown in FIG. 2. Amino acids at positions of RidA that are important for ligand binding and trimer formation include positions E120, C107, V18, K73, and E122. E120 in RidA, involved in ligand binding, is conserved across all paralogs. However, C107 in RidA, also important for ligand binding, is not conserved across all paralogs. Furthermore, the three residues V18, K73, and E122 that are important for trimer formation are also not conserved. Among these five amino acids, of the four that are not conserved across all paralogs, two of the them, amino acids at positions D76 and K123 of YjgH (corresponding to K73 and E122 of RidA), that are important for trimer formation show conservation between YjgH and YoaB. These two positions are highlighted in bold in FIG. 2.

A host cell that is engineered in accordance with the invention to overexpress an imine/enamine deaminase polypeptide, such as YjgH or YoaB, also overexpresses at least one enzyme involved in the synthesis of an amino or amino acid derivative, such as a lysine decarboxylase polypeptide; and/or an additional polypeptide that is involved in amino acid biosynthesis. Lysine decarboxylase and lysine biosynthesis polypeptides and nucleic acid sequences are available in the art.

The invention employs various routine recombinant nucleic acid techniques. Generally, the nomenclature and the laboratory procedures in recombinant DNA technology described below are commonly employed in the art. Many manuals that provide direction for performing recombinant DNA manipulations are available, e.g., Sambrook & Russell, Molecular Cloning, A Laboratory Manual (3rd Ed, 2001); and Current Protocols in Molecular Biology (Ausubel, et al., John Wiley and Sons, New York, 2009-2014).

Polynucleotides Encoding Imine/Enamine Deaminase Polypeptides

Various polynucleotides have been shown to encode polypeptides that catalyze the release of ammonia and reduce the levels of imine and enamine (e.g., yoaB or yjgH from *E. coli*).

Imine/enamine deaminase nucleic acid and polypeptide sequences suitable for use in the invention include imine/enamine deaminase nucleic acid sequences that encode an imine/enamine deaminase polypeptide as illustrated by SEQ ID NO:10 or SEQ ID NO:12, or biologically active variants that share substantial identity with SEQ ID NO:10 or SEQ ID NO:12. In some embodiments, such a substantially identical variant has at least 70%, or at least 75%, 80%, 85%, or 90% identity to SEQ ID NO:10 or SEQ ID NO:12, or an alternative imine/enamine deaminase polypeptide, e.g., a homolog of SEQ ID NO:10 or SEQ ID NO:12. In some embodiments, a substantially identical variant, as determined with reference to the *E. coli* YjgH protein sequence SEQ ID NO:12, comprises an acidic amino acid residue at position 121, an acidic residue at position 76, and a basic amino acid residue at position 123. In some embodiments, a substantially identical variant, as determined with reference to the *E. coli* YjgH protein sequence SEQ ID NO:12, comprises a D at position 76, an E at position 121, and a K at position 123. In some embodiments, a variant has at least 90%, or at least 95% identity to the amino acid sequence of SEQ ID NO:10 or SEQ ID NO:12. As used herein, the term "variant" encompasses biologically active polypeptides having one or more substitutions, deletions, or insertions relative to an imine/enamine deaminase polypeptide reference sequence, such as SEQ ID NO:10 or 12. Thus, the term "variant" includes biologically active fragments as well as substitution variants.

In some embodiments, a host is genetically modified in accordance with the invention to express a YoaB polypeptide. An illustrative sequence is provided as SEQ ID NO:10. In some embodiments, the host cell is genetically modified to express a YoaB polypeptide that has at least 90% identity, or at least 95% identity to SEQ ID NO:10 and increases lysine and/or cadaverine production by at least 20%, or greater compared to a counterpart strain that is not engineered to overexpress the YoaB polypeptide. In some embodiments, the YoaB polypeptide hast at least 70% identity or at least 75% identity to SEQ ID NO:10. In some embodiments, the YoaB polypeptide hast at least 80% identity or at least 85% identity to SEQ ID NO:10.

In some embodiments, a host is genetically modified in accordance with the invention to express a YjgH polypeptide. An illustrative sequence is provided as SEQ ID NO:12. In some embodiments, the host cell is genetically modified to express a YjgH polypeptide that has at least 90% identity, or at least 95% identity, to SEQ ID NO:12 and increases lysine and/or cadaverine production by at least 20%, or greater compared to a counterpart strain that is not engineered to overexpress the YjgH polypeptide. In some embodiments, the YjgH polypeptide has at least 70% identity or at least 75% identity to SEQ ID NO:12. In some embodiments, the YjgH polypeptide hast at least 80% identity or at least 85% identity to SEQ ID NO:12.

Imine/enamine deaminase polypeptide activity can be assessed using any number of assays, including assays that evaluate the production of an amino acid or an amino acid-derived compound. In some embodiments, the production of lysine or cadaverine production is measured. Illustrative assays are provided in the examples section. In some embodiments, cadaverine production is measured in $E.\ coli$ modified to co-express LysC, DapA, LysA, Asd, DapB, AspC, and CadA and the variant of YoaB or YjgH to be tested, or another imine/enamine deaminase polypeptide to be tested. The following is an illustrative assay that is used to assess production of lysine and/or cadaverine. $E.\ coli$ are modified to express LysC, DapA, LysA, Asd, DapB, AspC, and CadA and the variant to be tested. The genes may be individually introduced into $E.\ coli$, or introduced in one or more operons. For examples, LysC, DapA, LysA, Asd, DapB, and AspC may be encoded by a synthetic operon present in one plasmid and CadA and a candidate variant may be encoded by a separate plasmid. Each plasmid has a unique antibiotic-resistance selectable marker. Antibiotic-resistant colonies are selected and cultured. For example, cultures are grown overnight at 37° C. in 3 mL of medium containing 4% glucose, 0.1% $KH_2PO_4$, 0.1% $MgSO_4$, 1.6% $(NH_4)_2SO_4$, 0.001% $FeSO_4$, 0.001% $MnSO_4$, 0.2% yeast extract, 0.05% L-methionine, 0.01% L-threonine, 0.005% L-isoleucine, and appropriate antibiotics for selection. The following day, each culture is inoculated into 50 mL of fresh medium with 30 g/L of glucose, 0.7% $Ca(HCO_3)_2$, antibiotic(s), and grown for 72 hours at 37° C., at which point the concentration of lysine is determined. Lysine or cadaverine can be quantified using NMR. Yield can be calculated by dividing the molar amount of lysine or cadaverine produced by the molar amount of glucose added. An imine/enamine deaminase polypeptide for use in the invention increases the yield of lysine or cadaverine. Alternatively, colonies are evaluated for increased production of another lysine derivative.

In some embodiments, a YoaB or YjgH polypeptide increases lysine or cadaverine production by at least 10%, at least 20%, at least 30%, at least 40%, at least 50% or greater, when expressed in a host cell compared to a counterpart host cell of the same strain that comprises the same genetic modifications other than the modification to overexpress the YoaB or YjgH polypeptide. In some embodiments, YoaB or YjgH polypeptide increases lysine or cadaverine production by at least 10%, at least 20%, at least 30%, at least 40%, at least 50% or greater, when expressed in a host cell that is modified to overexpress a lysine decarboxylase, an aspartate kinase, a dihydrodipicolinate synthase, a diaminopimelate decarboxylase, an aspartate semialdehyde dehydrogenase, a dihydropicolinate reductase, and an aspartate transaminase; compared to a counterpart host cell of the same strain that comprises the modification to overexpress the lysine decarboxylase, the aspartate kinase, the dihydrodipicolinate synthase, the diaminopimelate decarboxylase, the aspartate semialdehyde dehydrogenase, the dihydropicolinate reductase, and the aspartate transaminase, but does not overexpress the YoaB or YjgH polypeptide.

Isolation or generation of imine/enamine deaminase polynucleotide sequences can be accomplished by a number of techniques. Such techniques will be discussed in the context of imine/enamine deaminase genes. However, one of skill understands that the same techniques can be used to isolate and express other desired genes. In some embodiments, oligonucleotide probes based on the sequences disclosed here can be used to identify the desired polynucleotide in a cDNA or genomic DNA library from a desired bacterial species. Probes may be used to hybridize with genomic DNA or cDNA sequences to isolate homologous genes in the same or different plant species.

Alternatively, the nucleic acids of interest can be amplified from nucleic acid samples using routine amplification techniques. For instance, PCR may be used to amplify the sequences of the genes directly from mRNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Appropriate primers and probes for identifying an imine/enamine deaminase polynucleotide in bacteria can be generated from comparisons of the sequences provided herein. For a general overview of PCR see PCR Protocols: A Guide to Methods and Applications. (Innis, M, Gelfand, D., Sninsky, J. and White, T., eds.), Academic Press, San Diego (1990). Illustrative primer sequences are shown in the Table of Primers in the Examples section.

Nucleic acid sequences encoding an imine/enamine deaminase polypeptide for use in the disclosure includes genes and gene products identified and characterized by techniques such as hybridization and/or sequence analysis using illustrative nucleic acid sequences, e.g., SEQ ID NO:9 or SEQ ID NO:11. In some embodiments, a host cell is genetically modified by introducing a nucleic acid sequence having at least 60% identity, or at least 70%, 75%, 80%, 85%, or 90% identity, or 100% identity, to a polynucleotide comprising SEQ ID NO:9 or SEQ ID NO:11.

Nucleic acid sequences encoding an imine/enamine deaminase polypeptide that confers increased production of an amino acid, e.g., lysine, or an amino acid-derived product, e.g., cadaverine, to a host cell, may additionally be codon-optimized for expression in a desired host cell. Methods and databases that can be employed are known in the art. For example, preferred codons may be determined in relation to codon usage in a single gene, a set of genes of common function or origin, highly expressed genes, the codon frequency in the aggregate protein coding regions of the whole organism, codon frequency in the aggregate protein coding regions of related organisms, or combinations thereof. See e.g., Henaut and Danchin in "*Escherichia coli* and *Salmonella*," Neidhardt, et al. Eds., ASM Pres, Washington D.C. (1996), pp. 2047-2066; Nucleic Acids Res. 20:2111-2118; Nakamura et al., 2000, Nucl. Acids Res. 28:292).

Preparation of Recombinant Vectors

Recombinant vectors for expression of an imine/enamine deaminase polypeptide can be prepared using methods well known in the art. For example, a DNA sequence encoding an imine/enamine deaminase polypeptide (described in further detail below), can be combined with transcriptional and other regulatory sequences which will direct the transcription of the sequence from the gene in the intended cells, e.g., bacterial cells such as *E. coli*. In some embodiments, an expression vector that comprises an expression cassette that comprises the gene encoding the imine/enamine deaminase polypeptide further comprises a promoter operably linked to the imine/enamine deaminase gene. In other embodiments, a promoter and/or other regulatory elements that direct transcription of the imine/enamine deaminase gene are endogenous to the host cell and an expression cassette comprising the imine/enamine deaminase gene is introduced, e.g., by homologous recombination, such that the exogenous gene is operably linked to an endogenous promoter and is expression driven by the endogenous promoter.

As noted above, expression of the gene encoding an imine/enamine deaminase polypeptide can be controlled by a number of regulatory sequences including promoters, which may be either constitutive or inducible; and, optionally, repressor sequences, if desired. Examples of suitable promoters, especially in a bacterial host cell, are the promoters obtained from the *E. coli* lac operon and other promoters derived from genes involved in the metabolism of other sugars, e.g., galactose and maltose. Additional examples include promoters such as the trp promoter, bla promoter bacteriophage lambda PL, and T5. In addition, synthetic promoters, such as the tac promoter (U.S. Pat. No. 4,551,433), can be used. Further examples of promoters include *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes. Suitable promoters are also described in Ausubel and Sambrook & Russell, both supra. Additional promoters include promoters described by Jensen & Hammer, *Appl. Environ. Microbiol.* 64:82, 1998; Shimada, et al., *J. Bacteriol.* 186:7112, 2004; and Miksch et al., *Appl. Microbiol. Biotechnol.* 69:312, 2005.

In some embodiments, a promoter that influences expression of a native imine/enamine deaminase polypeptide may be modified to increase expression. For example, an endogenous YoaB or YjgH promoter may be replaced by a promoter that provides for increased expression compared to the native promoter.

An expression vector may also comprise additional sequences that influence expression of a gene encoding the imine/enamine deaminase polypeptide. Such sequences include enhancer sequences, a ribosome binding site, or other sequences such as transcription termination sequences, and the like.

A vector expressing a nucleic acid encoding an imine/enamine deaminase polypeptide of the invention may be an autonomously replicating vector, i.e., a vector which exists as an extrachromosomal entity, the replication of which is independent of chromosomal replication, e.g., a plasmid, an extrachromosomal element, a mini-chromosome, or an artificial chromosome. The vector may contain any means for assuring self-replication. Alternatively, the vector may be one which, when introduced into the host, is integrated into the genome and replicated together with the chromosome(s) into which it has been integrated. Thus, an expression vector may additionally contain an element(s) that permits integration of the vector into the host's genome.

An expression vector of the invention preferably contains one or more selectable markers which permit easy selection of transformed hosts. For example, an expression vector may comprise a gene that confers antibiotic resistance (e.g., ampicillin, kanamycin, chloramphenicol or tetracycline resistance) to the recombinant host organism, e.g., a bacterial cell such as *E. coli*.

Although any suitable expression vector may be used to incorporate the desired sequences, readily available bacterial expression vectors include, without limitation: plasmids such as pSClOl, pBR322, pBBR1MCS-3, pUR, pET, pEX, pMRlOO, pCR4, pBAD24, p15a, pACYC, pUC, e.g., pUC18 or pUC19, or plasmids derived from these plasmids; and bacteriophages, such as Ml 3 phage and λ phage. One of ordinary skill in the art, however, can readily determine through routine experimentation whether any particular expression vector is suited for any given host cell. For example, the expression vector can be introduced into the host cell, which is then monitored for viability and expression of the sequences contained in the vector.

Expression vectors of the invention may be introduced into the host cell using any number of well-known methods, including calcium chloride-based methods, electroporation, or any other method known in the art.

Host Cells

The present invention provides for a genetically modified host cell that is engineered to overexpress an exogenous imine/enamine deaminase polypeptide. Such a host cell may comprise a nucleic acid encoding a heterologous imine/enamine deaminase peptide, including any non-naturally occurring imine/enamine deaminase polypeptide variant; or may be genetically modified to overexpress a native imine/enamine deaminase polypeptide relative to a wildtype host cell.

A genetically modified host strain of the present invention typically comprises at least one additional genetic modification to enhance production of an amino acid or amino acid derivative relative to a control strain that does not have the one additional genetic modification, e.g., a wildtype strain or a cell of the same strain without the one additional genetic modification. An "additional genetic modification to enhance production of an amino acid or amino acid derivative" can be any genetic modification. In some embodiments, the genetic modification is the introduction of a polynucleotide that expresses an enzyme involved in the synthesis of the amino acid or amino acid derivative. In some embodiments, the host cell comprises multiple modifications to increase production, relative to a wildtype host cell, of an amino acid or amino acid derivative.

In some aspects, genetic modification of a host cell to overexpress an imine/enamine deaminase polypeptide is performed in conjunction with modifying the host cell to overexpress a lysine decarboxylase polypeptide and/or one or more lysine biosynthesis polypeptides.

A lysine decarboxylase refers to an enzyme that converts L-lysine into cadaverine. The enzyme is classified as E.C. 4.1.1.18. Lysine decarboxylase polypeptides are well characterized enzymes, the structures of which are well known in the art (see, e.g., Kanjee, et al., EMBO J. 30: 931-944, 2011; and a review by Lemmonier & Lane, Microbiology 144; 751-760, 1998; and references described therein). The EC number for lysine decarboxylase is 4.1.1.18. Illustrative lysine decarboxylase sequences are CadA homologs from *Klebsiella* sp., WP 012968785.1; *Enterobacter aerogenes*, YP 004592843.1; *Salmonella enterica*, WP 020936842.1; *Serratia* sp., WP 033635725.1; and *Raoultella ornithinolytica*, YP 007874766.1; and LdcC homologs from *Shigella* sp., WP 001020968.1; *Citrobacter* sp., WP 016151770.1; and *Salmonella enterica*, WP 001021062.1. As used herein, a lysine decarboxylase includes variants of native lysine decarboxylase enzymes that have lysine decarboxylase enzymatic activity. Additional lysine decarboxylase enzymes are described in PCT/CN2014/080873 and PCT/CN2015/072978.

In some embodiments, a host cell may be genetically modified to express one or more polypeptides that affect lysine biosynthesis. Examples of lysine biosynthesis polypeptides include the *E. coli* genes SucA, Ppc, AspC, LysC, Asd, DapA, DapB, DapD, ArgD, DapE, DapF, LysA, Ddh, PntAB, CyoABE, GadAB, YbjE, GdhA, GltA, SucC, GadC, AcnB, PflB, ThrA, AceA, AceB, GltB, AceE, SdhA, MurE, SpeE, SpeG, PuuA, PuuP, and YgjG, or the corresponding genes from other organisms. Such genes are known in the art (see, e.g., Shah et al., *J. Med. Sci.* 2:152-157, 2002; Anastassiadia, S. *Recent Patents on Biotechnol.* 1: 11-24, 2007). See, also, Kind, et al., *Appl. Microbiol. Biotechnol.* 91: 1287-1296, 2011 for a review of genes involved in cadaverine production. Illustrative genes encoding lysine biosynthesis polypeptides are provided below.

| Protein | Gene | EC Number | GenBank Accession No. |
|---|---|---|---|
| α-ketoglutarate dehydrogenase (SucA) | sucA | 1.2.4.2 | YP_489005.1 |
| Phosphoenolpyruvate carboxylase (PPC) | ppc | 4.1.1.31 | AAC76938.1 |
| aspartate transaminase (AspC) | aspC | 2.6.1.1 | AAC74014.1 |
| aspartate kinase (LysC) | lysC | 2.7.2.4 | NP_418448.1 |
| aspartate semialdehyde dehydrogenase (Asd) | asd | 1.2.1.11 | AAC76458.1 |
| dihydrodipicolinate synthase (DapA) | dapA | 4.3.3.7 | NP_416973.1 |
| dihydropicolinate reductase (DapB) | dapB | 1.17.1.8 | AAC73142.1 |
| tetrahydrodipicoinate succinylase (DapD) | dapD | 2.3.1.117 | AAC73277.1 |
| N-succinyldiaminopimelate aminotransferase (ArgD) | argD | 2.6.1.11 | AAC76384.1 |
| N-succinyl-L-diaminopimelate deacylase (DapE) | dapE | 3.5.1.18 | AAC75525.1 |
| diaminopimelate epimerase (DapF) | dapF | 5.1.1.7 | AAC76812.2 |

-continued

| Protein | Gene | EC Number | GenBank Accession No. |
|---|---|---|---|
| diaminopimelate decarboxylase (LysA) | lysA | 4.1.1.20 | AAC75877.1 |
| meso-diaminopimelate dehydrogenase (Ddh) | ddh | NA | P04964.1 |
| pyridine nucleotide transhydrogenase (PntAB) | pntAB | NA | AAC74675.1, AAC74674.1 |
| cytochrome O oxidase (CyoABE) | cyoABE | 1.10.3.10 | AAC73535.1, AAC73534.1, AAC73531.1 |
| glutamate decarboxylase (GadAB) | gadAB | 4.1.1.15 | AAC76542.1, AAC74566.1 |
| L-amino acid efflux transporter (YbjE) | ybjE | NA | AAC73961.2 |
| glutamate dehydrogenase (GdhA) | gdhA | 1.4.1.4 | AAC74831.1 |
| citrate synthase (GltA) | gltA | 2.3.3.1/ 2.3.3.16 | AAC73814.1 |
| succinyl-coA synthase (SucC) | sucC | 6.2.1.5 | AAC73822.1 |
| glutamate-GABA antiporter (GadC) | gadC | NA | AAC74565.1 |
| aconitase B (AcnB) | acnB | 4.2.1.99 | AAC73229.1 |
| pyruvate-formate lyase (PflB) | pflB | NA | AAC73989.1 |
| aspartate kinase/homoserine dehydrogenase (ThrA) | thrA | 2.7.2.4 | AAC73113.1 |
| isocitrate lyase (AceA) | aceA | 4.1.3.1 | AAC76985.1 |
| malate synthase (AceB) | aceB | 2.3.3.9 | AAC76984.1 |
| glutmate synthase (GltB) | gltB | 1.4.1.13 | AAC76244.2 |
| pyruvate dehydrogenase (AceE) | aceE | 1.2.4.1 | AAC73225.1 |
| succinate dehydrogenase (SdhA) | sdhA | 1.3.5.1 | AAC73817.1 |
| UDP-N-acetylmuramoyl-L-alanyl-D-glutamate:meso-diaminopimelate ligase (MurE) | murE | 6.3.2.13 | AAC73196.1 |
| putrescine/cadaverine aminopropyltransferase (SpeE) | speE | 2.5.1.16 | AAC73232.1 |
| spermidine acetyltransferase (SpeG) | speG | NA | AAC74656.1 |
| glutamate-putrescine/glutamate-cadaverine ligase (PuuA) | puuA | NA | AAC74379.2 |
| putrescine importer (PuuP) | puuP | NA | AAC74378.2 |
| putrescine/cadaverine aminotransferase (YgjG) | ygjG | 2.6.1.82 | AAC76108.3 |

In some embodiments, a host cell is genetically modified to express a lysine decarboxylase, an aspartate kinase, a dihydrodipicolinate synthase, a diaminopimelate decarboxylase, an aspartate semialdehyde dehydrogenase, a dihydropicolinate reductase, and an aspartate transaminase. Additional modifications may also be incorporated into the host cell.

In some embodiments, a host cell may be genetically modified to attenuate or reduce the expression of one or more polypeptides that affect lysine biosynthesis. Examples of such polypeptides include the *E. coli* genes Pck, Pgi, DeaD, CitE, MenE, PoxB, AceA, AceB, AceE, RpoC, and ThrA, or the corresponding genes from other organisms. Such genes are known in the art (see, e.g., Shah et al., *J. Med. Sci.* 2:152-157, 2002; Anastassiadia, S. *Recent Patents on Biotechnol.* 1: 11-24, 2007). See, also, Kind, et al., *Appl. Microbiol. Biotechnol.* 91: 1287-1296, 2011 for a review of genes attenuated to increase cadaverine production. Illustrative genes encoding polypeptides whose attenuation increases lysine biosynthesis are provided below.

| Protein | Gene | EC Number | GenBank Accession No. |
|---|---|---|---|
| PEP carboxykinase (Pck) | pck | 4.1.1.49 | NP_417862 |
| Glucose-6-phosphate isomerase (Pgi) | pgi | 5.3.1.9 | NP_418449 |

-continued

| Protein | Gene | EC Number | GenBank Accession No. |
|---|---|---|---|
| DEAD-box RNA helicase (DeaD) | deaD | | NP_417631 |
| citrate lyase (CitE) | citE | 4.1.3.6/4.1.3.34 | NP_415149 |
| o-succinylbenzoate-CoA ligase (MenE) | menE | 6.2.1.26 | NP_416763 |
| pyruvate oxidase (PoxB) | poxB | 1.2.2.2 | NP_415392 |
| isocitrate lyase (AceA) | aceA | 4.1.3.1 | NP_418439 |
| malate synthase A (AceB) | aceB | 2.3.3.9 | NP_418438 |
| pyruvate dehydrogenase (aceE) | aceE | 1.2.4.1 | NP_414656 |
| RNA polymerase b' subunit (RpoC) | rpoC | 2.7.7.6 | NP_418415 |
| aspartokinase I (ThrA) | thrA | 2.7.2.4/1.1.1.3 | NP_414543 |

Nucleic acids encoding a lysine decarboxylase or a lysine biosynthesis polypeptide may be introduced into the host cell along with the imine/enamine deaminase polynucleotide, e.g., encoded on a single expression vector, or introduced in multiple expression vectors at the same time. Alternatively, the host cell may be genetically modified to overexpress lysine decarboxylase or one or more lysine biosynthesis polypeptides before or after the host cell is genetically modified to overexpress the imine/enamine deaminase polypeptide.

In alternative embodiments, a host cell that overexpresses a naturally occurring imine/enamine deaminase polypeptide can be obtained by other techniques, e.g., by mutagenizing cells, e.g., E. coli cells, and screening cells to identify those that an imine/enamine deaminase polypeptide, e.g., YoaB or YjhG, at a higher level compared to the cell prior to mutagenesis.

A host cell comprising an imine/enamine deaminase polypeptide as described herein is a bacterial host cell. In typical embodiments, the bacterial host cell is a Gram-negative bacterial host cell. In some embodiments of the invention, the bacterium is an enteric bacterium. In some embodiments of the invention, the bacterium is a species of the genus Corynebacterium, Escherichia, Pseudomonas, Zymomonas, Shewanella, Salmonella, Shigella, Enterobacter, Citrobacter, Cronobacter, Erwinia, Serratia, Proteus, Hafnia, Yersinia, Morganella, Edwardsiella, or Klebsiella taxonomical classes. In some embodiments, the host cells are members of the genus Escherichia, Hafnia, or Corynebacterium. In some embodiments, the host cell is an Escherichia coli, Hafnia alvei, or Corynebacterium glutamicum host cell.

In some embodiments, the host cell is a gram-positive bacterial host cell, such as a Bacillus sp., e.g., Bacillus subtilis or Bacillus licheniformis; or another Bacillus sp. such as B. alcalophilus, B. aminovorans, B. amyloliquefaciens, B. caldolyticus, B. circulans, B. stearothermophilus, B. thermoglucosidasius, B. thuringiensis or B. vulgatis.

Host cells modified in accordance with the invention can be screened for increased production of lysine or a lysine derivative, such as cadaverine, as described herein.
Methods of Producing Lysine or a Lysine Derivative.

A host cell genetically modified to overexpress an imine/enamine deaminase polypeptide can be employed to produce lysine or a derivative of lysine. In some embodiments, the host cell produces cadaverine. To produce lysine or the lysine derivative, a host cell genetically modified to overexpress an imine/enamine deaminase polypeptide as described herein can be cultured under conditions suitable to allow expression of the polypeptide and expression of genes that encode the enzymes that are used to produce lysine or the lysine derivative. A host cell modified in accordance with the invention provides a higher yield of lysine or lysine derivatives relative to a non-modified counterpart host cell that expresses the imine/enamine deaminase polypeptide at native levels.

Host cells may be cultured using well known techniques (see, e.g., the illustrative conditions provided in the examples section).

The lysine or lysine derivative can then be separated and purified using known techniques. Lysine or lysine derivatives, e.g., cadaverine, produced in accordance with the invention may then be used in any known process, e.g., to produce a polyamide.

In some embodiments, lysine may be converted to caprolactam using chemical catalysts or by using enzymes and chemical catalysts.

The present invention will be described in greater detail by way of specific examples. The following examples are offered for illustrative purposes, and are not intended to limit the invention in any manner. Those of skill in the art will readily recognize a variety of noncritical parameters, which can be changed or modified to yield essentially the same results.

EXAMPLES

The following examples are offered to illustrate, but not to limit the claimed invention.

Example 1: Construction of Plasmid Vectors that Encode CadA

A plasmid vector containing wild-type E. coli cadA (SEQ ID NO: 1), which encodes the lysine decarboxylase CadA (SEQ ID NO: 2), was amplified from the E. coli MG1655 K12 genomic DNA using the PCR primers cadA-F and cadA-R, digested using the restriction enzymes SacI and BamHI, and ligated into pSTV28 to generate the plasmid pCIB39. The 5' sequence upstream of the cadA gene was optimized using the PCR primers cadA-F2 and cadA-R2 to create pCIB40. The SacI restriction site was added back to pCIB40 using the SacI-F and SacI-R primers to create pCIB41.

Example 2: Construction of Plasmid Vectors Expressing a Gene Encoding a Imine/Enamine Deaminase The E. coli gene, ridA (SEQ ID NO: 3), that encodes an imine/enamine deaminase, RidA (SEQ ID NO: 4), was amplified from the E. coli MG1655 K12 genomic DNA using the PCR primers ridA-F and ridA-R, digested with the restriction enzymes SacI and BamHI, and ligated into pCIB41 plasmid vector also digested with SacI and BamHI to create pCIB144. Similarly, rutC (SEQ ID NO: 5), which encodes RutC (SEQ ID NO: 6), was cloned into pCIB41 using the primers rutC-F and rutC-R to create the plasmid pCIB174; and tdcF (SEQ ID NO: 7), which encodes TdcF (SEQ ID NO: 8), was cloned into pCIB41 using the primers tdcF-F and tdcF-R to create the plasmid pCIB175. YoaB (SEQ ID NO: 9), which encodes YoaB (SEQ ID NO: 10), was cloned into pCIB41 using the primers yoaB-F and yoaB-R to create the plasmid pCIB177; and yjgH (SEQ ID NO: 11), that encodes YjgH (SEQ ID NO: 12), was cloned into pCIB41 using the primers yjgH-F and yjgH-R to create the plasmid pCIB194.

Example 3: Construction of Plasmid Vectors Co-Expressing Synthetic Operon I that Contains Three Proteins (LysC, DapA, LysA) from the Lysine Biosynthetic Pathway Three genes from *E. coli*, lysC, dapA, and lysA, encode proteins involved in the *E. coli* lysine biosynthetic pathway: aspartate kinase (LysC or AKIII, encoded by lysC), dihydrodipicolinate synthase (DapA or DHDPS, encoded by dapA), and diaminopimelate decarboxylase (LysA, encoded by lysA). The three genes were cloned into a plasmid vector and the three proteins, LysC (SEQ ID NO: 13), DapA (SEQ ID NO: 14), and LysA (SEQ ID NO: 15) were overexpressed in *E. coli*. The gene lysC was amplified from the *E. coli* MG1655 K12 genomic DNA using the primers lysC-F and lysC-R, and the amplified fragment was digested using SacI and BamHI, and ligated into pUC18 to create pCIB7. The gene dapA was amplified from the *E. coli* MG1655 K12 genomic DNA using the primers dapA-F and dapA-R, and the amplified fragment was digested using BamHI and XbaI, and ligated into pCIB7 to create pCIB8. The gene lysA was amplified from the *E. coli* MG1655 K12 genomic DNA using the primers lysA-F and lysA-R, and the amplified fragment was digested using XbaI and SalI, and ligated into pCIB8 to create pCIB9. The three-gene operon was amplified from pCIB9 using the primers lysC-F and lysA-R. The amplified product was digested using SacI and SalI, and the digested fragment was ligated into pCIB10 to create pCIB32.

To construct pCIB10, the synthetic promoter sequence (SEQ ID NO:22) was synthesized using the PCR primers psyn-1 and psyn-2. Primer psyn-1 contains the promoter sequence and a sequence homologous to pUC18, and primer psyn-2 contains a sequence homologous to pUC18. These two PCR primers were used to amplify a portion of pUC18 that includes the multi-cloning site from the plasmid inserted downstream of the synthetic promoter sequence. Restriction enzymes EcoRI and SacI were used to digest the amplified DNA containing the synthetic promoter, which was further ligated into pUC18 to construct pCIB10.

Example 4: Construction of Plasmid Vectors Co-Expressing Various Aspartokinases. Various Aspartokinases were Expressed in Order to Increase Lysine Production Two pairs of mutations were chosen that enabled the *E. coli* LysC to have an increased feedback resistance to lysine. The gene encoding the first mutant, LysC-1 (M318I, G323D) (SEQ. ID NO: 16) was constructed using the primers 318-F, 318-R, 323-F, 323-R. The genes encoding LysC-1 (M318I, G323D) was cloned into pCIB32 and replaced the wild-type *E. coli* aspartokinase, LysC, to create the plasmids pCIB43. The aspartokinase from *Streptomyces* strains that is capable of producing polylysine was previously suggested, but not proven, to be more feedback resistant to lysine compared to *E. coli* aspartokinase. As such, the aspartokinase gene from *Streptomyces lividans* was codon optimized, synthesized, and cloned in place of wild-type lysC in pCIB32 in order to create the plasmid pCIB55 using the primers SlysC-F and SlysC-R. The resulting aspartokinase protein that was expressed was named S-LysC (SEQ ID NO: 17).

Example 5: Construction of Plasmid Vectors Co-Expressing Synthetic Operon II that Contains Three Proteins (Asd, DapB, DapD, AspC) from the Lysine Biosynthetic Pathway Next, the expression of four additional genes, asd, dapB, dapD, and aspC, which are involved in the lysine biosynthetic pathway of *E. coli*, was enhanced. These genes encode the following enzymes: aspartate semialdehyde dehydrogenase (Asd (SEQ ID NO: 18), encoded by asd), dihydrodipicolinate reductase (DapB or DHDPR (SEQ ID NO: 19), encoded by dapB), tetrahydrodipicolinate succinylase (DapD (SEQ ID NO: 20), encoded by dapD), and aspartate transaminase (AspC (SEQ ID NO: 21), encoded by aspC). The gene asd was amplified from the *E. coli* MG1655 K12 genomic DNA using the primers asd-F and asd-R, and the amplified fragment was digested using SacI and BamHI, and ligated into pUC18 to create pCIB12. The gene dapB was amplified from the *E. coli* MG1655 K12 genomic DNA using the primers dapB-F and dapB-R, and the amplified fragment was digested using BamHI and XbaI, and ligated into pCIB12 to create pCIB13. The gene dapD was amplified from the *E. coli* MG1655 K12 genomic DNA using the primers dapD-F and dapD-R, and the amplified fragment was digested using XbaI and SalI, and ligated into pCIB13 to create pCIB14. Similarly, the gene aspC was amplified from the *E. coli* MG1655 K12 genomic DNA using the primers aspC-F and aspC-R, and the amplified fragment was digested using XbaI and SalI, and ligated into pCIB13 to create pCIB31.

Example 6: Construction of Plasmid Vectors Co-Expressing Synthetic Operons I and II that Contain Proteins from the Lysine Biosynthetic Pathway Synthetic Operon I was further adjusted using primers lysC-rbs2-F and lysC-rbs2-R to modify pCIB43 and create the plasmid pCIB378. Synthetic Operon II was further adjusted using the primers asd-rbs2-F and asd-rbs2-R to modify pCIB31 and create the plasmid pCIB380. pCIB380 was further modified using the primers SacI-F2, SacI-R2, ApaI-F, and ApaI-R in order to add the restriction enzyme sites for ApaI and SacI to pCIB380 in order to create the plasmid pCIB393. The two synthetic operons, Synthetic Operon I and Synthetic Operon II, consisting of the genes lysC, dapA, lysA, asd, dapB, and aspC were combined into a single vector. The operon from pCIB378 consisting of the genes lysC, dapA, and lysA was amplified using the primers LAL2-SacI-F and LAL2-ApaI-R, digested using the restriction enzymes SacI and ApaI, and ligated into pCIB393 in order to create the plasmid pCIB394.

Example 7: Production of Lysine from *E. coli* Over-Expressing Synthetic Operons I and II and an Imine/Enamine Deaminase

*E. coli* MG1655 K12 was transformed with one of the following combination of plasmids: pCIB394 and pSTV28, pCIB394 and pCIB144, pCIB394 and pCIB174, pCIB394 and pCIB175, pCIB394 and pCIB177, or pCIB394 and pCIB194. Three single colonies from each transformation were grown overnight at 37° C. in 3 mL of medium containing 4% glucose, 0.1% $KH_2PO_4$, 0.1% $MgSO_4$, 1.6% $(NH_4)_2SO_4$, 0.001% $FeSO_4$, 0.001% $MnSO_4$, 0.2% yeast extract, 0.05% L-methionine, 0.01% L-threonine, 0.005% L-isoleucine, ampicillin (100 µg/mL), and chloramphenicol (20 µg/mL). The following day, each culture was inoculated into 100 mL of fresh medium with 30 g/L of glucose, 0.7% $Ca(HCO_3)_2$, ampicillin (100 µg/mL), and chloramphenicol (20 µg/mL). The culture was grown for 72 hours at 37° C., at which point the concentration of lysine in each culture was determined (Table 1).

TABLE 1

Production of lysine by E. coli strains containing Synthetic Operons I and II, and an imine/enamine deaminase.

| Strain | Protein(s) | Lysine (g/L) |
|---|---|---|
| MG1655 | none | n.d. |
| pCIB394 & pSTV28 | LysC, DapA, LysA, Asd, DapB, AspC | 6.0 ± 0.4 |
| pCIB394 & pCIB144 | LysC, DapA, LysA, Asd, DapB, AspC, RidA | 6.1 ± 0.3 |
| pCIB394 & pCIB174 | LysC, DapA, LysA, Asd, DapB, AspC, RutC | 5.9 ± 0.3 |
| pCIB394 & pCIB175 | LysC, DapA, LysA, Asd, DapB, AspC, TdcF | 6.2 ± 0.4 |
| pCIB394 & pCIB177 | LysC, DapA, LysA, Asd, DapB, AspC, YoaB | 7.3 ± 0.2 |
| pCIB394 & pCIB 194 | LysC, DapA, LysA, Asd, DapB, AspC, YjgH | 7.1 ± 0.3 | n.d.: none detected

As shown in Table 1, the overproduction of different imine/enamine deaminases affected lysine production differently. The overproduction of RidA did not lead to any observable change in lysine production. Similarly, the overproduction of two RidA paralogs RutC and TdcF also did not lead to any change in lysine production. Surprisingly, the overproduction of two RidA paralogs did increase lysine production from 6 g/L to 7.3 g/L for a system overproducing YoaB, and 7.1 g/L for a system overproducing YjgH.

Example 8: Construction of Plasmid Vectors Encoding a Lysine Decarboxylase and an Imine/Enamine Deaminase The yoaB gene on pCIB177 was modified to remove the BamHI and SphI restriction sites using the primer pairs rmvBamHI-F and rmvBamHI-R, and rmvSphI-F and rmvSphI-R. The modified yoaB gene was amplified using the primers yoaB-F2 and yoaB-R2, the amplified fragment was digested using the restriction enzymes BamHI and SphI, and ligated into pCIB41 to form the plasmid pCIB201. Similarly, pCIB194 was modified to remove the BamHI and SphI restriction sites using the primer pairs rmvBamHI-F2 and rmvBamHI-R2, rmvSphI-F2 and rmvSphI-R2, and rmvSphI-F3 and rmvSphI-R3. The modified yjgH gene was amplified using the primers yjgH-F2 and yjgH-R2, the amplified fragment was digested using the restriction enzymes BamHI and SphI, and ligated into pCIB41 to form the plasmid pCIB208.

Example 9: Production of Lysine from E. coli Co-Overexpressing Genes that Encode Imine/Enamine Deaminase Proteins and Lysine Synthetic Operons I and II E. coli MG1655 K12 was transformed with one of the following combination of plasmids: pCIB394 and pSTV28, pCIB394 and pCIB41, pCIB394 and pCIB201, or pCIB394 and pCIB208. Three single colonies from each transformation were grown overnight at 37° C. in 3 mL of medium containing 4% glucose, 0.1% $KH_2PO_4$, 0.1% $MgSO_4$, 1.6% $(NH_4)_2SO_4$, 0.001% $FeSO_4$, 0.001% $MnSO_4$, 0.2% yeast extract, 0.05% L-methionine, 0.01% L-threonine, 0.005% L-isoleucine, ampicillin (100 µg/mL), and chloramphenicol (20 µg/mL). The following day, each culture was inoculated into 100 mL of fresh medium with 30 g/L of glucose, 0.7% $Ca(HCO_3)_2$, ampicillin (100 µg/mL), and chloramphenicol (20 µg/mL). The culture was grown for 72 hours at 37° C., at which point the concentration of lysine and cadaverine in each culture was determined (Table 2).

TABLE 2

Production of lysine and cadaverine by E. coli strains that contain the lysine Synthetic Operons I and II and overproduce a lysine decarboxylase and an imine/enamine deaminase.

| Strain | Protein(s) | Lysine (g/L) | Cadaverine (g/L) |
|---|---|---|---|
| MG1655 | none | n.d. | n.d. |
| pCIB394 & pSTV28 | LysC, DapA, LysA, Asd, DapB, AspC | 6.1 ± 0.3 | n.d. |
| pCIB394 & pCIB41 | LysC, DapA, LysA, Asd, DapB, AspC, CadA | 0.5 ± 0.2 | 3.0 ± 0.2 |
| pCIB394 & pCIB201 | LysC, DapA, LysA, Asd, DapB, AspC, CadA, YoaB | 0.5 ± 0.2 | 3.9 ± 0.3 |
| pCIB394 & pCIB208 | LysC, DapA, LysA, Asd, DapB, AspC, CadA, YjgH | 0.5 ± 0.2 | 4.1 ± 0.2 | n.d.: none detected

As shown in Table 2, overproduction of CadA led to the production of cadaverine. Furthermore, the overproduction of imine/enamine deaminase further increased cadaverine production from 3.0 g/L to 3.9 g/L for YoaB and 4.1 g/L for YjgH.

Although the foregoing invention has been described in some detail by way of illustration and example for purposes of clarity of understanding, one of skill in the art will appreciate that certain changes and modifications may be practiced within the scope of the appended claims. All publications, patents, accession numbers, and patent applications cited herein are incorporated herein by reference to disclose and describe the methods and/or materials in connection with which the publications are cited. Where a conflict exists between the instant application and a reference provided herein, the instant application shall dominate.

Table of plasmids used in Examples

| Protein(s) Overexpressed | Plasmid |
|---|---|
| none | pSTV28 |
| CadA | pCIB41 |
| RidA | pCIB144 |
| RutC | pCIB174 |
| TdcF | pCIB175 |
| YoaB | pCIB177 |
| YjgH | pCIB194 |
| LysC, DapA, LysA, Asd, DapB, AspC | pCIB394 |
| CadA, YoaB | pCIB201 |
| CadA, YjgH | pCIB208 |

Table of primer sequences used in Examples.

| Name | Sequence (5'-3') |
|---|---|
| cadA-F | ggcgagctcacacaggaaacagaccatgaacgt tattgcaatattgaatc |
| cadA-R | ggcggatccccacttcccttgtacgagctaatt atttttgctttcttctttc |
| cadA-F2 | atttcacacaggaaacagctatgaacgttattg caatattgaatcac |
| cadA-R2 | agctgtttcctgtgtgaaat |

Table of primer sequences used in Examples.

| Name | Sequence (5'-3') |
|---|---|
| SacI-F | ggcgagctcctcctgtgtgaaattgttatccgctc |
| SacI-R | ggcgagctcatgaacgttattgcaatattgaatc |
| ridA-F | ggcgagctcatgagcaaaactatcgcgacg |
| ridA-R | ggcggatccttagcgacgaacagcgatcg |
| rutC-F | ggcgagctcatgccaaaatccgtaattattcc |
| rutC-R | ggcggatcctcacttggcgatatgcgcaa |
| tdcF-F | ggcgagctcatgaaaaagattatcgaaacgcaac |
| tdcF-R | ggcggatccttacgcactacgtactgcga |
| yoaB-F | ggcgagctcatgactatcgttcgtatcgatgctg |
| yoaB-R | ggcggatccttacaccgcagccacaatct |
| yjgH-F | ggcgagctcatggtagaaagaaccgctgttttc |
| yjgH-R | ggcggatcctattgcttactgctcaggatg |
| lysC-F | ggcgagctcacacaggaaacagaccatgtctgaaattgttgtctcc |
| lysC-R | ggcggatccttactcaaacaaattactatgcag |
| dapA-F | ggcggatcccacacaggaaacagaccatgttcacgggaagtattgtc |
| dapA-R | ggctctagattacagcaaaccggcatgc |
| lysA-F | ggctctagaacacaggaaacagaccatgccacattcactgttcagc |
| lysA-R | ggcgtcgacttaaagcaattccagcgccag |
| 318-F | cagcctgaatatactgcattctc |
| 318-R | gagaatgcagtatattcaggctg |
| 323-F | gcattctcgcgatttcctcg |
| 323-R | cgaggaaatcgcgagaatgc |
| SlysC-F | ggcgagctcacacaggaaacagaccatgggcttagttgtgcagaaa |
| SlysC-R | ggcggatccttaacgacctgtgccgccata |
| asd-F | ggcgagctcacacaggaaacagaccatgaaaaatgttggttttatcgg |
| asd-R | ggcggatccttacgccagttgacgaagc |
| dapB-F | ggcacacaggaaacagaccatgcatgatgcaaacatccg |
| dapB-R | ggctctagattacaaattattgagatcaagtacatctc |
| dapD-F | ggctctagaacacaggaaacagaccatgcagcagttacagaacat |
| dapD-R | ggcgcatgcttagtcgatggtacgcagca |
| aspC-F | ggctctagaacacaggaaacagaccatgtttgaaacattaccgcc |
| aspC-R | ggcgcatgcgacctcgaggtagtcgacttacagcactgccacaatcg |
| lysC-rbs2-F | atttcacacaggaaacagctatgtctgaaattgttgtctcca |
| lysC-rbs2-R | agctgtttcctgtgtgaaat |
| asd-rbs2-F | atttcacacaggaaacagctatgaaaaatgttggttttatcggctg |
| asd-rbs2-R | agctgtttcctgtgtgaaat |
| SacI-F2 | ggcgagctctcccctgattctgtggataa |
| SacI-R2 | ggcgagctcagcaaaaggccaggaaccgt |
| ApaI-F | ggcgggcccgtattaccgcctttgagtgag |
| ApaI-R | ggcgggcccacagaatcaggggagagctc |
| LAL2-SacI-F | ggcgagctcgttggccgattcattaatgc |
| LAL2-ApaI-R | ggcgggccctttaaagcaattccagcgccag |
| rmvBamHI-F | tgcggtgtaaggttcctctagag |
| rmvBamHI-R | ctctagaggaaccttacaccgca |
| rmvSphI-F | gacctgcaggcttgcaagcttg |
| rmvSphI-R | caagcttgcaagcctgcaggtc |
| yoaB-F2 | ggcggatcccacacaggaggagctcatgactatcgttcgtatcgatg |
| yoaB-R2 | ggcgcatgctcattcgccattcaggctgc |
| rmvSphI-F2 | catttgataatttacatgcgacccctg |
| rmvSphI-R2 | cagggtcgcatgtaaattatcaaatg |
| yjgH-F2 | ggcggatcccacacaggaggagctcatggtagaaagaaccgctgtt |
| yjgH-R2 | ggcgcatgctattgcttactgctcaggga |
| psyn-1 | ggcgaattcagtttattatgacatgtagtgaggggctggtataatgagctcggtacccggggat |
| psyn-2 | ggcagtactcaaccaagtcattctgagaatagtg |

Illustrative sequences
Escherichia coli cadA nucleic acid sequence
SEQ ID NO: 1
ATGAACGTTATTGCAATATTGAATCACATGGGGGTTTATTTTAAAGAAGA

ACCCATCCGTGAACTTCATCGCGCGCTTGAACGTCTGAACTTCCAGATTG

TTTACCCGAACGACCGTGACGACTTATTAAAACTGATCGAAAACAATGCG

CGTCTGTGCGGCGTTATTTTTGACTGGGATAAATATAATCTCGAGCTGTG

CGAAGAAATTAGCAAAATGAACGAGAACCTGCCGTTGTACGCGTTCGCTA

ATACGTATTCCACTCTCGATGTAAGCCTGAATGACCTGCGTTTACAGATT

AGCTTCTTTGAATATGCGCTGGGTGCTGCTGAAGATATTGCTAATAAGAT

CAAGCAGACCACTGACGAATATATCAACACTATTCTGCCTCCGCTGACTA

-continued

```
AAGCACTGTTTAAATATGTTCGTGAAGGTAAATATACTTTCTGTACTCCT
GGTCACATGGGCGGTACTGCATTCCAGAAAAGCCCGGTAGGTAGCCTGTT
CTATGATTTCTTTGGTCCGAATACCATGAAATCTGATATTTCCATTTCAG
TATCTGAACTGGGTTCTCTGCTGGATCACAGTGGTCCACACAAAGAAGCA
GAACAGTATATCGCTCGCGTCTTTAACGCAGACCGCAGCTACATGGTGAC
CAACGGTACTTCCACTGCGAACAAAATTGTTGGTATGTACTCTGCTCCAG
CAGGCAGCACCATTCTGATTGACCGTAACTGCCACAAATCGCTGACCCAC
CTGATGATGATGAGCGATGTTACGCCAATCTATTTCCGCCCGACCCGTAA
CGCTTACGGTATTCTTGGTGGTATCCCACAGAGTGAATTCCAGCACGCTA
CCATTGCTAAGCGCGTGAAAGAAACACCAAACGCAACCTGGCCGGTACAT
GCTGTAATTACCAACTCTACCTATGATGGTCTGCTGTACAACACCGACTT
CATCAAGAAAACACTGGATGTGAAATCCATCCACTTTGACTCCGCGTGGG
TGCCTTACACCAACTTCTCACCGATTTACGAAGGTAAATGCGGTATGAGC
GGTGGCCGTGTAGAAGGGAAAGTGATTTACGAAACCCAGTCCACTCACAA
ACTGCTGGCGGCGTTCTCTCAGGCTTCCATGATCCACGTTAAAGGTGACG
TAAACGAAGAAACCTTTAACGAAGCCTACATGATGCACACCACCACTTCT
CCGCACTACGGTATCGTGGCGTCCACTGAAACCGCTGCGGCGATGATGAA
AGGCAATGCAGGTAAGCGTCTGATCAACGGTTCTATTGAACGTGCGATCA
AATTCCGTAAAGAGATCAAACGTCTGAGAACGGAATCTGATGGCTGGTTC
TTTGATGTATGGCAGCCGGATCATATCGATACGACTGAATGCTGGCCGCT
GCGTTCTGACAGCACCTGGCACGGCTTCAAAAACATCGATAACGAGCACA
TGTATCTTGACCCGATCAAAGTCACCCTGCTGACTCCGGGGATGGAAAAA
GACGGCACCATGAGCGACTTTGGTATTCCGGCCAGCATCGTGGCGAAATA
CCTCGACGAACATGGCATCGTTGTTGAGAAAACCGGTCCGTATAACCTGC
TGTTCCTGTTCAGCATCGGTATCGATAAGACCAAAGCACTGAGCCTGCTG
CGTGCTCTGACTGACTTTAAACGTGCGTTCGACCTGAACCTGCGTGTGAA
AAACATGCTGCCGTCTCTGTATCGTGAAGATCCTGAATTCTATGAAAACA
TGCGTATTCAGGAACTGGCTCAGAATATCCACAAACTGATTGTTCACCAC
AATCTGCCGGATCTGATGTATCGCGCATTTGAAGTGCTGCCGACGATGGT
AATGACTCCGTATGCTGCATTCCAGAAAGAGCTGCACGGTATGACCGAAG
AAGTTTACCTCGACGAAATGGTAGGTCGTATTAACGCCAATATGATCCTT
CCGTACCCGCCGGGAGTTCCTCTGGTAATGCCGGGTGAAATGATCACCGA
AGAAAGCCGTCCGGTTCTGGAGTTCCTGCAGATGCTGTGTGAAATCGGCG
CTCACTATCCGGGCTTTGAAACCGATATTCACGGTGCATACCGTCAGGCT
GATGGCCGCTATACCGTTAAGGTATTGAAAGAAGAAAGCAAAAAATAA.
```

CadA polypeptide sequence
SEQ ID NO: 2
MNVIAILNHMGVYFKEEPIRELHRALERLNFQIVYPNDRDDLLKLIENNA
RLCGVIFDWDKYNLELCEEISKMNENLPLYAFANTYSTLDVSLNDLRLQI
SFFEYALGAAEDIANKIKQTTDEYINTILPPLTKALFKYVREGKYTFCTP
GHMGGTAFQKSPVGSLFYDFFGPNTMKSDISISVSELGSLLDHSGPHKEA
EQYIARVFNADRSYMVTNGTSTANKIVGMYSAPAGSTILIDRNCHKSLTH
LMMMSDVTPIYFRPTRNAYGILGGIPQSEFQHATIAKRVKETPNATWPVH
AVITNSTYDGLLYNTDFIKKTLDVKSIHFDSAWVPYTNFSPIYEGKCGMS
GGRVEGKVIYETQSTHKLLAAFSQASMIHVKGDVNEETFNEAYMMHTTTS
PHYGIVASTETAAAMMKGNAGKRLINGSIERAIKFRKEIKRLRTESDGWF
FDVWQPDHIDTTECWPLRSDSTWHGFKNIDNEHMYLDPIKVTLLTPGMEK
DGTMSDFGIPASIVAKYLDEHGIVVEKTGPYNLLFLFSIGIDKTKALSLL
RALTDFKRAFDLNLRVKNMLPSLYREDPEFYENMRIQELAQNIHKLIVHH
NLPDLMYRAFEVLPTMVMTPYAAFQKELHGMTEEVYLDEMVGRINANMIL
PYPPGVPLVMPGEMITEESRPVLEFLQMLCEIGAHYPGFETDIHGAYRQA
DGRYTVKVLKEESKK.

E. coli ridA nucleic acid sequence
SEQ ID NO: 3
```
ATGAGCAAAACTATCGCGACGGAAAATGCACCGGCAGCTATCGGTCCTTA
CGTACAGGGCGTTGATCTGGGCAATATGATCATCACCTCCGGTCAGATCC
CGGTAAATCCGAAAACGGGCGAAGTACCGGCAGACGTCGCTGCACAGGCA
CGTCAGTCGCTGGATAACGTAAAAGCGATCGTCGAAGCCGCTGGCCTGAA
AGTGGGCGACATCGTTAAAACTACCGTGTTTGTAAAAGATCTGAACGACT
TCGCAACCGTAAACGCCACTTACGAAGCCTTCTTCACCGAACACAACGCC
ACCTTCCCGGCACGTTCTTGCGTTGAAGTTGCCCGTCTGCCGAAAGACGT
GAAGATTGAGATCGAAGCGATCGCTGTTCGTCGCTAA.
```

RidA polypeptide sequence
SEQ ID NO: 4
MSKTIATENAPAAIGPYVQGVDLGNMIITSGQIPVNPKTGEVPADVAAQA
RQSLDNVKAIVEAAGLKVGDIVKTTVFVKDLNDFATVNATYEAFFTEHNA
TFPARSCVEVARLPKDVKIEIEAIAVRR.

E. coli rutC nucleic acid sequence
SEQ ID NO: 5
```
ATGCCAAAATCCGTAATTATTCCCGCTGGCAGCAGCGCACCGCTGGCCCC
CTTCGTTCCCGGCACGCTGGCTGATGGCGTGGTGTATGTCTCCGGTACGC
TGGCTTTTGATCAACATAATAACGTGCTGTTTGCCGATGACCCAAAGGCG
CAAACCCGCCACGTTCTGGAAACTATCCGCAAGGTGATCGAGACGGCGGG
TGGCACGATGGCGGATGTGACCTTCAACAGCATCTTTATTACCGACTGGA
AAAATTACGCCGCGATTAACGAAATCTACGCCGAGTTTTTTCCGGGTGAT
AAACCGGCGCGATTCTGCATTCAGTGCGGACTGGTAAAACCTGACGCGCT
GGTGGAAATCGCCACAATTGCGCATATCGCCAAGTGA.
```

RutC polypeptide sequence
SEQ ID NO: 6
MPKSVIIPAGSSAPLAPFVPGTLADGVVYVSGTLAFDQHNNVLFADDPKA
QTRHVLETIRKVIETAGGTMADVTFNSIFITDWKNYAAINEIYAEFFPGD
KPARFCIQCGLVKPDALVEIATIAHIAK.

E. coli tdcF nucleic acid sequence
SEQ ID NO: 7
ATGAAAAAGATTATCGAAACGCAACGTGCCCCAGGCGCAATCGGCCCTTA
TGTTCAGGGCGTTGATTTAGGCAGCATGGTCTTCACCTCCGGGCAAATAC
CGGTTTGCCCACAGACCGGTGAGATCCCGGCTGATGTGCAAGATCAGGCG

```
CGTTTAAGCCTCGAAAACGTCAAAGCGATCGTGGTTGCTGCCGGGCTGAG
CGTGGGCGATATCATCAAGATGACCGTGTTTATCACCGATCTGAATGATT
TTGCCACCATCAACGAAGTCTATAAGCAGTTCTTCGATGAGCATCAGGCG
ACCTATCCGACCCGGAGCTGTGTGCAGGTCGCGCGTTTGCCGAAAGATGT
GAAGCTGGAAATTGAAGCCATCGCAGTACGTAGTGCGTAA.
```
TdcF polypeptide sequence
SEQ ID NO: 8
```
MKKIIETQRAPGAIGPYVQGVDLGSMVFTSGQIPVCPQTGEIPADVQDQA
RLSLENVKAIVVAAGLSVGDIIKMTVFITDLNDFATINEVYKQFFDEHQA
TYPTRSCVQVARLPKDVKLEIEAIAVRSA.
```
E. coli yoaB nucleic acid sequence
SEQ ID NO: 9
```
ATGACTATCGTTCGTATCGATGCTGAAGCCCGCTGGTCTGATGTAGTAAT
CCACAACAACACGCTCTACTACACTGGTGTACCGGAAAACCTCGACGCCG
ATGCCTTTGAGCAAACCGCCAACACGCTGGCACAGATTGACGCCGTGCTG
GAAAAACAGGGCAGCAATAAATCGAGCATTCTGGATGCCACCATTTTCCT
GGCCGATAAAAACGACTTCGCGGCGATGAATAAAGCGTGGGATGCTTGGG
TTGTCGCGGGTCATGCGCCGGTGCGCTGCACGGTACAAGCGGGTTTGATG
AACCCGAAGTATAAAGTTGAAATTAAGATTGTGGCTGCGGTGTAA.
```
YoaB polypeptide sequence
SEQ ID NO: 10
```
MTIVRIDAEARWSDVVIHNNTLYYTGVPENLDADAFEQTANTLAQIDAVL
EKQGSNKSSILDATIFLADKNDFAAMNKAWDAWVVAGHAPVRCTVQAGLM
NPKYKVEIKIVAAV.
```
E. coli yjgH nucleic acid sequence
SEQ ID NO: 11
```
ATGGTAGAAAGAACCGCTGTTTTCCCTGCTGGCCGACATTCACTATATGC
TGAGCATCGTTATTCTGCGGCTATTCGTTCCGGCGATTTGCTGTTTGTTT
CCGGGCAAGTAGGAAGTCGAGAGGACGGAACACCAGAACCCGATTTTCAG
CAACAAGTCAGACTGGCATTTGATAATTTGCATGCGACCCTGGCAGCTGC
GGGATGCACTTTTGACGATATCATTGATGTTACGAGCTTCCATACCGATC
CAGAAAACCAATTTGAAGACATCATGACGGTGAAAAATGAAATATTTAGC
GCCCCACCTTATCCAAACTGGACGGCGGTGGGTGTTACATGGCTGGCAGG
CTTTGATTTTGAAATTAAAGTGATAGCGCGCATCCCTGAGCAGTAA.
```
YjgH polypeptide sequence
SEQ ID NO: 12
```
MVERTAVFPAGRHSLYAEHRYSAAIRSGDLLFVSGQVGSREDGTPEPDFQ
QQVRLAFDNLHATLAAAGCTFDDIIDVTSFHTDPENQFEDIMTVKNEIFS
APPYPNWTAVGVTWLAGFDFEIKVIARIPEQ.
```
LysC polypeptide sequence
SEQ ID NO: 13
```
MSEIVVSKFGGTSVADFDAMNRSADIVLSDANVRLVVLSASAGITNLLVA
LAEGLEPGERFEKLDAIRNIQFAILERLRYPNVIREEIERLLENITVLAE
AAALATSPALTDELVSHGELMSTLLFVEILRERDVQAQWFDVRKVMRTND
RFGRAEPDIAALAELAALQLLPRLNEGLVITQGFIGSENKGRTTTLGRGG
SDYTAALLAEALHASRVDIWTDVPGIYTTDPRVVSAAKRIDEIAFAEAAE
MATFGAKVLHPATLLPAVRSDIPVFVGSSKDPRAGGTLVCNKTENPPLFR
ALALRRNQTLLTLHSLNMLHSRGFLAEVFGILARHNISVDLITTSEVSVA
LTLDTTGSTSTGDTLLTQSLLMELSALCRVEVEEGLALVALIGNDLSKAC
GVGKEVFGVLEPFNIRMICYGASSHNLCFLVPGEDAEQVVQKLHSNLFE.
```
DapA polypeptide sequence
SEQ ID NO: 14
```
MFTGSIVAIVTPMDEKGNVCRASLKKLIDYHVASGTSAIVSVGTTGESAT
LNHDEHADVVMMTLDLADGRIPVIAGTGANATAEAISLTQRFNDSGIVGC
LTVTPYYNRPSQEGLYQHFKAIAEHTDLPQILYNVPSRTGCDLLPETVGR
LAKVKNIIGIKEATGNLTRVNQIKELVSDDFVLLSGDDASALDFMQLGGH
GVISVTANVAARDMAQMCKLAAEGHFAEARVINQRLMPLHNKLFVEPNPI
PVKWACKELGLVATDTLRLPMTPITDSGRETVRAALKHAGLL.
```
LysA polypeptide sequence
SEQ ID NO: 15
```
MPHSLFSTDTDLTAENLLRLPAEFGCPVWVYDAQIIRRQIAALKQFDVVR
FAQKACSNIHILRLMREQGVKVDSVSLGEIERALAAGYNPQTHPDDIVFT
ADVIDQATLERVSELQIPVNAGSVDMLDQLGQVSPGHRVWLRVNPGFGHG
HSQKTNTGGENSKHGIWYTDLPAALDVIQRHHLQLVGIHMMHIGSGVDYAH
LEQVCGAMVRQVIEFGQDLQAISAGGGLSVPYQQGEEAVDTEHYYGLWNA
AREQIARHLGHPVKLEIEPGRFLVAQSGVLITQVRSVKQMGSRHFVLVDA
GFNDLMRPAMYGSYHHISALAADGRSLEHAPTVETVVAGPLCESGDVFTQ
QEGGNVETRALPEVKAGDYLVLHDTGAYGASMSSNYNSRPLLPEVLFDNG
QARLIRRRQTIEELLALELL.
```
LysC-1 M318I, G323D polypeptide sequence
SEQ ID NO: 16
```
MSEIVVSKFGGTSVADFDAMNRSADIVLSDANVRLVVLSASAGITNLLVA
LAEGLEPGERFEKLDAIRNIQFAILERLRYPNVIREEIERLLENITVLAE
AAALATSPALTDELVSHGELMSTLLFVEILRERDVQAQWFDVRKVMRTND
RFGRAEPDIAALAELAALQLLPRLNEGLVITQGFIGSENKGRTTTLGRGG
SDYTAALLAEALHASRVDIWTDVPGIYTTDPRVVSAAKRIDEIAFAEAAE
MATFGAKVLHPATLLPAVRSDIPVFVGSSKDPRAGGTLVCNKTENPPLFR
ALALRRNQTLLTLHSLNILHSRDFLAEVFGILARHNISVDLITTSEVSVA
LTLDTTGSTSTGDTLLTQSLLMELSALCRVEVEEGLALVALIGNDLSKAC
GVGKEVFGVLEPFNIRMICYGASSHNLCFLVPGEDAEQVVQKLHSNLFE.
```
S-LysC polypeptide sequence
SEQ ID NO: 17
```
MGLVVQKYGGSSVADAEGIKRVAKRIVEAKKNGNQVVAVVSAMGDTTDEL
IDLAEQVSPIPAGRELDMLLTAGERISMALLAMAIKNLGHEAQSFTGSQA
GVITDSVHNKARIIDVTPGRIRTSVDEGNVAIVAGFQGVSQDSKDITTLG
RGGSDTTAVALAAALDADVCEIYTDVDGVFTADPRVVPKAKKIDWISFED
MLELAASGSKVLLHRCVEYARRYNIPIHVRSSFSGLQGTWVSSEPIKQGE
KHVEQALISGVAHDTSEAKVTVVGVPDKPGEAAAIFRAIADAQVNIDMVV
QNVSAASTGLTDISFTLPKSEGRKAIDALEKNRPGIGFDSLRYDDQIGKI
SLVGAGMKSNPGVTADFFTALSDAGVNIELISTSEIRISVVTRKDDVNEA
VRAVHTAFGLDSDSDEAVVYGGTGR.
```

Asd polypeptide sequence
SEQ ID NO: 18
MKNVGFIGWRGMVGSVLMQRMVEERDFDAIRPVFFSTSQLGQAAPSFGGT
TGTLQDAFDLEALKALDIIVTCQGGDYTNEIYPKLRESGWQGYWIDAASS
LRMKDDAIIILDPVNQDVITDGLNNGIRTFVGGNCTVSLMLMSLGGLFAN
DLVDWVSVATYQAASGGGARHMRELLTQMGHLYGHVADELATPSSAILDI
ERKVTTLTRSGELPVDNFGVPLAGSLIPWIDKQLDNGQSREEWKGQAETN
KILNTSSVIPVDGLCVRVGALRCHSQAFTIKLKKDVSIPTVEELLAAHNP
WAKVVPNDREITMRELTPAAVTGTLTTPVGRLRKLNMGPEFLSAFTV
GDQ.

DapB polypeptide sequence
SEQ ID NO: 19
MHDANIRVAIAGAGGRMGRQLIQAALALEGVQLGAALEREGSSLLGSDAG
ELAGAGKTGVTVQSSLDAVKDDFDVFIDFTRPEGTLNHLAFCRQHGKGMV
IGTTGFDEAGKQAIRDAAADIAIVFAANFSVGVNVMLKLLEKAAKVMGDY
TDIEIIEAHHRHKVDAPSGTALAMGEAIAHALDKDLKDCAVYSREGHTGE
RVPGTIGFATVRAGDIVGEHTAMFADIGERLEITHKASSRMTFANGAVRS
ALWLSGKESGLFDMRDVLDLNNL.

DapD polypeptide sequence
SEQ ID NO: 20
MQQLQNIIETAFERRAEITPANADTVTREAVNQVIALLDSGALRVAEKID
GQWVTHQWLKKAVLLSFRINDNQVIEGAESRYFDKVPMKFADYDEARFQK
EGFRVVPPAAVRQGAFIARNTVLMPSYVNIGAYVDEGTMVDTWATVGSCA
QIGKNVHLSGGVGIGGVLEPLQANPTIIEDNCFIGARSEVVEGVIVEEGS
VISMGVYIGQSTRIYDRETGEIHYGRVPAGSVVVSGNLPSKDGKYSLYCA
VIVKKVDAKTRGKVGINELLRTID.

AspC polypeptide sequence
SEQ ID NO: 21
MFENITAAPADPILGLADLFRADERPGKINLGIGVYKDETGKTPVLTSVK
KAEQYLLENETTKNYLGIDGIPEFGRCTQELLFGKGSALINDKRARTAQT
PGGTGALRVAADFLAKNTSVKRVWVSNPSWPNHKSVFNSAGLEVREYAYY
DAENHTLDFDALINSLNEAQAGDVVLFHGCCHNPTGIDPTLEQWQTLAQL
SVEKGWLPLFDFAYQGFARGLEEDAEGLRAFAAMHKELIVASSYSKNFGL
YNERVGACTLVAADSETVDRAFSQMKAAIRANYSNPPAHGASVVATILSN
DALRAIWEQELTDMRQRIQRMRQLFVNTLQEKGANRDFSFIIKQNGMFSF
SGLTKEQVLRLREEFGVYAVASGRVNVAGMTPDNMAPLCEAIVAVL.

synthetic promoter nucleic acid sequence
SEQ ID NO: 22
AGTTTATTCTTGACATGTAGTGAGGGGGCTGGTATAAT.

---

What is claimed is:

1. A genetically modified host cell that enhances removal of imine and enamine compounds, said host cell comprising an exogenous polynucleotide that encodes and overexpresses an imine/enamine deaminase polypeptide that increases the amount of an amino acid or amino acid derivative compared to a host cell that has not been modified to express the exogenous polynucleotide, wherein the host cell is of the genus *Escherichia*, the amino acid is lysine, and the amino acid derivative is cadaverine, and wherein the imine/enamine deaminase polypeptide:
   (i) has at least 95% identity to the amino acid sequence of SEQ ID NO: 12; or
   (ii) comprises the amino acid sequence of SEQ ID NO: 12.

2. The genetically modified host cell of claim 1, wherein the imine/enamine deaminase polypeptide:
   (i) is heterologous to the host cell, or
   (ii) comprises an amino acid sequence that is native to the host cell.

3. The genetically modified host cell of claim 1, wherein the exogenous polynucleotide is:
   (i) contained in an expression vector introduced into the cell, wherein the expression vector comprises the exogenous polynucleotide operably linked to a promoter, or
   (ii) integrated into the host chromosome.

4. The genetically modified host cell of claim 1, wherein the host cell overexpresses:
   (i) an exogenous lysine decarboxylase polypeptide, and/or
   (ii) one or more exogenous lysine biosynthesis polypeptides, wherein the exogenous lysine biosynthesis polypeptide is an aspartate kinase, a dihydrodipicolinate synthase, a diaminopimelate decarboxylase, an aspartate semialdehyde dehydrogenase, a dihydropicolinate reductase, or an aspartate transaminase.

5. The genetically modified host cell of claim 4, wherein the exogenous lysine decarboxylase polypeptide is a CadA polypeptide.

6. The genetically modified host cell of claim 4, wherein the aspartate kinase, dihydrodipicolinate synthase, diaminopimelate decarboxylase, aspartate semialdehyde dehydrogenase, adihydropicolinate reductase, or aspartate transaminase is a LysC, DapA, LysA, Asd, DapB, or AspC polypeptide.

7. The genetically modified host cell of claim 1, wherein the host cell is *Escherichia coli*.

8. A method of engineering the host cell of claim 1 to increase production of lysine or cadaverine, comprising:
   introducing the polynucleotide that encodes the imine/enamine deaminase polypeptide in the host cell;
   culturing the host cell under conditions in which the imine/enamine deaminase polypeptide is expressed, and selecting the host cell that has an increase in the amount of lysine or cadaverine produced compared to the host cell that is not modified to introduce the polynucleotide encoding the imine/enamine deaminase polypeptide.

9. The method of claim 8, wherein the host cell is genetically modified to overexpress:
   (i) an exogenous lysine decarboxylase polypeptide, and/or
   (ii) one or more exogenous lysine biosynthesis polypeptides, wherein the lysine biosynthesis polypeptide is an aspartate kinase, a dihydrodipicolinate synthase, a diaminopimelate decarboxylase, an aspartate semialdehyde dehydrogenase, a dihydropicolinate reductase, or an aspartate transaminase.

10. The method of claim 9, wherein the lysine decarboxylase polypeptide is a CadA polypeptide.

11. The method of claim 9, wherein the host cell is *Escherichia coli*.

12. A method of producing lysine or cadaverine in an increased amount, comprising:
   culturing the host cell of claim 1 under conditions in which the imine/enamine deaminase polypeptide is expressed; and
   isolating the lysine or cadaverine.

13. The method of claim 12, further comprising isolating the lysine or cadaverine.

14. The genetically modified host cell of claim 1, wherein overexpression of the imine/enamine deaminase polypeptide increases the amount of the lysine or cadaverine by at least 10% compared to the host cell that has not been modified to express the exogenous polynucleotide.

* * * * *

SEQUENCE LISTING

<160> NUMBER OF SEQ ID NOS: 89

<210> SEQ ID NO 1
<211> LENGTH: 2148
<212> TYPE: DNA
<213> ORGANISM: Escherichia coli

<400> SEQUENCE: 1

```
atgaacgtta ttgcaatatt gaatcacatg ggggtttatt ttaaagaaga acccatccgt      60
gaacttcatc gcgcgcttga acgtctgaac ttccagattg tttacccgaa cgaccgtgac     120
gacttattaa aactgatcga aaacaatgcg cgtctgtgcg gcgttatttt tgactgggat     180
aaatataatc tcgagctgtg cgaagaaatt agcaaaatga cgagaaacct gccgttgtac     240
gcgttcgcta atacgtattc cactctcgat gtaagcctga atgacctgcg tttacagatt     300
agcttctttg aatatgcgct gggtgctgct gaagatattg ctaataagat caagcagacc     360
actgacgaat atatcaacac tattctgcct ccgctgacta agcactgtt  taaatatgtt     420
cgtgaaggta aatatacttt ctgtactcct ggtcacatgg gcggtactgc attccagaaa     480
agcccggtag gtagcctgtt ctatgatttc tttggtccga ataccatgaa atctgatatt     540
tccatttcag tatctgaact gggttctctg ctggatcaca gtggtccaca caaagaagca     600
gaacagtata tcgctcgcgt ctttaacgca gaccgcagct acatggtgac caacggtact     660
tccactgcga acaaaattgt tggtatgtac tctgctccag caggcagcac cattctgatt     720
gaccgtaact gccacaaatc gctgacccac ctgatgatga tgagcgatgt tacgccaatc     780
tatttccgcc cgacccgtaa cgcttacggt attcttggtg gtatcccaca gagtgaattc     840
cagcacgcta ccattgctaa gcgcgtgaaa gaaacaccaa acgcaacctg gccggtacat    900
```

```
gctgtaatta ccaactctac ctatgatggt ctgctgtaca acaccgactt catcaagaaa      960
acactggatg tgaaatccat ccactttgac tccgcgtggg tgccttacac caacttctca     1020
ccgatttacg aaggtaaatg cggtatgagc ggtggccgtg tagaagggaa agtgatttac     1080
gaaacccagt ccactcacaa actgctggcg gcgttctctc aggcttccat gatccacgtt     1140
aaaggtgacg taaacgaaga aacctttaac gaagcctaca tgatgcacac caccacttct     1200
ccgcactacg gtatcgtggc gtccactgaa accgctgcgg cgatgatgaa aggcaatgca     1260
ggtaagcgtc tgatcaacgg ttctattgaa cgtgcgatca aattccgtaa agagatcaaa     1320
cgtctgagaa cggaatctga tggctggttc tttgatgtat ggcagccgga tcatatcgat     1380
acgactgaat gctggccgct gcgttctgac agcacctggc acggcttcaa aacatcgat     1440
aacgagcaca tgtatcttga cccgatcaaa gtcaccctgc tgactccggg gatgaaaaa     1500
gacggcacca tgagcgactt ggtattccg gccagcatcg tggcgaaata cctcgacgaa     1560
catggcatcg ttgttgagaa aaccggtccg tataacctgc tgttcctgtt cagcatcggt     1620
atcgataaga ccaaagcact gagcctgctg cgtgctctga ctgactttaa acgtgcgttc     1680
gacctgaacc tgcgtgtgaa aaacatgctg ccgtctctgt atcgtgaaga tcctgaattc     1740
tatgaaaaca tgcgtattca ggaactggct cagaatatcc acaaactgat tgttcaccac     1800
aatctgccgg atctgatgta tcgcgcattt gaagtgctgc cgacgatggt aatgactccg     1860
tatgctgcat tccagaaaga gctgcacggt atgaccgaag aagtttacct cgacgaaatg     1920
gtaggtcgta ttaacgccaa tatgatcctt ccgtacccgc cgggagttcc tctggtaatg     1980
ccgggtgaaa tgatcaccga agaaagccgt ccggttctgg agttcctgca gatgctgtgt     2040
gaaatcggcg ctcactatcc gggctttgaa accgatattc acggtgcata ccgtcaggct     2100
gatggccgct ataccgttaa ggtattgaaa gaagaaagca aaaaataa                  2148
```

<210> SEQ ID NO 2
<211> LENGTH: 715
<212> TYPE: PRT
<213> ORGANISM: Escherichia coli
<400> SEQUENCE: 2

```
Met Asn Val Ile Ala Ile Leu Asn His Met Gly Val Tyr Phe Lys Glu
1               5                   10                  15

Glu Pro Ile Arg Glu Leu His Arg Ala Leu Glu Arg Leu Asn Phe Gln
            20                  25                  30

Ile Val Tyr Pro Asn Asp Arg Asp Asp Leu Leu Lys Leu Ile Glu Asn
        35                  40                  45

Asn Ala Arg Leu Cys Gly Val Ile Phe Asp Trp Asp Lys Tyr Asn Leu
    50                  55                  60

Glu Leu Cys Glu Glu Ile Ser Lys Met Asn Glu Asn Leu Pro Leu Tyr
65                  70                  75                  80

Ala Phe Ala Asn Thr Tyr Ser Thr Leu Asp Val Ser Leu Asn Asp Leu
                85                  90                  95

Arg Leu Gln Ile Ser Phe Phe Glu Tyr Ala Leu Gly Ala Ala Glu Asp
            100                 105                 110

Ile Ala Asn Lys Ile Lys Gln Thr Thr Asp Glu Tyr Ile Asn Thr Ile
        115                 120                 125

Leu Pro Pro Leu Thr Lys Ala Leu Phe Lys Tyr Val Arg Glu Gly Lys
    130                 135                 140

Tyr Thr Phe Cys Thr Pro Gly His Met Gly Gly Thr Ala Phe Gln Lys
```

```
            145                 150                 155                 160
        Ser Pro Val Gly Ser Leu Phe Tyr Asp Phe Gly Pro Asn Thr Met
                        165                 170                 175

Lys Ser Asp Ile Ser Ile Ser Val Ser Glu Leu Gly Ser Leu Leu Asp
                        180                 185                 190

His Ser Gly Pro His Lys Glu Ala Glu Gln Tyr Ile Ala Arg Val Phe
                        195                 200                 205

Asn Ala Asp Arg Ser Tyr Met Val Thr Asn Gly Thr Ser Thr Ala Asn
                        210                 215                 220

Lys Ile Val Gly Met Tyr Ser Ala Pro Ala Gly Ser Thr Ile Leu Ile
        225                 230                 235                 240

Asp Arg Asn Cys His Lys Ser Leu Thr His Leu Met Met Met Ser Asp
                        245                 250                 255

Val Thr Pro Ile Tyr Phe Arg Pro Thr Arg Asn Ala Tyr Gly Ile Leu
                        260                 265                 270

Gly Gly Ile Pro Gln Ser Glu Phe Gln His Ala Thr Ile Ala Lys Arg
                        275                 280                 285

Val Lys Glu Thr Pro Asn Ala Thr Trp Pro Val His Ala Val Ile Thr
                        290                 295                 300

Asn Ser Thr Tyr Asp Gly Leu Leu Tyr Asn Thr Asp Phe Ile Lys Lys
        305                 310                 315                 320

Thr Leu Asp Val Lys Ser Ile His Phe Asp Ser Ala Trp Val Pro Tyr
                        325                 330                 335

Thr Asn Phe Ser Pro Ile Tyr Glu Gly Lys Cys Gly Met Ser Gly Gly
                        340                 345                 350

Arg Val Glu Gly Lys Val Ile Tyr Glu Thr Gln Ser Thr His Lys Leu
                        355                 360                 365

Leu Ala Ala Phe Ser Gln Ala Ser Met Ile His Val Lys Gly Asp Val
                        370                 375                 380

Asn Glu Glu Thr Phe Asn Glu Ala Tyr Met Met His Thr Thr Thr Ser
        385                 390                 395                 400

Pro His Tyr Gly Ile Val Ala Ser Thr Glu Thr Ala Ala Ala Met Met
                        405                 410                 415

Lys Gly Asn Ala Gly Lys Arg Leu Ile Asn Gly Ser Ile Glu Arg Ala
                        420                 425                 430

Ile Lys Phe Arg Lys Glu Ile Lys Arg Leu Arg Thr Glu Ser Asp Gly
                        435                 440                 445

Trp Phe Phe Asp Val Trp Gln Pro Asp His Ile Asp Thr Thr Glu Cys
                        450                 455                 460

Trp Pro Leu Arg Ser Asp Ser Thr Trp His Gly Phe Lys Asn Ile Asp
        465                 470                 475                 480

Asn Glu His Met Tyr Leu Asp Pro Ile Lys Val Thr Leu Leu Thr Pro
                        485                 490                 495

Gly Met Glu Lys Asp Gly Thr Met Ser Asp Phe Gly Ile Pro Ala Ser
                        500                 505                 510

Ile Val Ala Lys Tyr Leu Asp Glu His Gly Ile Val Val Glu Lys Thr
                        515                 520                 525

Gly Pro Tyr Asn Leu Leu Phe Leu Phe Ser Ile Gly Ile Asp Lys Thr
                        530                 535                 540

Lys Ala Leu Ser Leu Leu Arg Ala Leu Thr Asp Phe Lys Arg Ala Phe
        545                 550                 555                 560

Asp Leu Asn Leu Arg Val Lys Asn Met Leu Pro Ser Leu Tyr Arg Glu
                        565                 570                 575
```

Asp Pro Glu Phe Tyr Glu Asn Met Arg Ile Gln Glu Leu Ala Gln Asn
            580                 585                 590

Ile His Lys Leu Ile Val His His Asn Leu Pro Asp Leu Met Tyr Arg
        595                 600                 605

Ala Phe Glu Val Leu Pro Thr Met Val Met Thr Pro Tyr Ala Ala Phe
    610                 615                 620

Gln Lys Glu Leu His Gly Met Thr Glu Glu Val Tyr Leu Asp Glu Met
625                 630                 635                 640

Val Gly Arg Ile Asn Ala Asn Met Ile Leu Pro Tyr Pro Pro Gly Val
                645                 650                 655

Pro Leu Val Met Pro Gly Glu Met Ile Thr Glu Glu Ser Arg Pro Val
            660                 665                 670

Leu Glu Phe Leu Gln Met Leu Cys Glu Ile Gly Ala His Tyr Pro Gly
        675                 680                 685

Phe Glu Thr Asp Ile His Gly Ala Tyr Arg Gln Ala Asp Gly Arg Tyr
    690                 695                 700

Thr Val Lys Val Leu Lys Glu Glu Ser Lys Lys
705                 710                 715

<210> SEQ ID NO 3
<211> LENGTH: 387
<212> TYPE: DNA
<213> ORGANISM: Escherichia coli

<400> SEQUENCE: 3
atgagcaaaa ctatcgcgac ggaaaatgca ccggcagcta tcggtcctta cgtacagggc     60
gttgatctgg gcaatatgat catcacctcc ggtcagatcc cggtaaatcc gaaaacgggc    120
gaagtaccgg cagacgtcgc tgcacaggca cgtcagtcgc tggataacgt aaaagcgatc    180
gtcgaagccg ctggcctgaa agtgggcgac atcgttaaaa ctaccgtgtt tgtaaaagat    240
ctgaacgact tcgcaaccgt aaacgccact tacgaagcct tcttcaccga acacaacgcc    300
accttcccgg cacgttcttg cgttgaagtt gcccgtctgc cgaaagacgt gaagattgag    360
atcgaagcga tcgctgttcg tcgctaa                                        387

<210> SEQ ID NO 4
<211> LENGTH: 128
<212> TYPE: PRT
<213> ORGANISM: Escherichia coli

<400> SEQUENCE: 4

Met Ser Lys Thr Ile Ala Thr Glu Asn Ala Pro Ala Ala Ile Gly Pro
1               5                   10                  15

Tyr Val Gln Gly Val Asp Leu Gly Asn Met Ile Ile Thr Ser Gly Gln
            20                  25                  30

Ile Pro Val Asn Pro Lys Thr Gly Glu Val Pro Ala Asp Val Ala Ala
        35                  40                  45

Gln Ala Arg Gln Ser Leu Asp Asn Val Lys Ala Ile Val Glu Ala Ala
    50                  55                  60

Gly Leu Lys Val Gly Asp Ile Val Lys Thr Thr Val Phe Val Lys Asp
65                  70                  75                  80

Leu Asn Asp Phe Ala Thr Val Asn Ala Thr Tyr Glu Ala Phe Phe Thr
                85                  90                  95

Glu His Asn Ala Thr Phe Pro Ala Arg Ser Cys Val Glu Val Ala Arg
            100                 105                 110

Leu Pro Lys Asp Val Lys Ile Glu Ile Glu Ala Ile Ala Val Arg Arg
        115                 120                 125

<210> SEQ ID NO 5
<211> LENGTH: 387
<212> TYPE: DNA
<213> ORGANISM: Escherichia coli

<400> SEQUENCE: 5

```
atgccaaaat ccgtaattat tcccgctggc agcagcgcac cgctggcccc cttcgttccc      60
ggcacgctgg ctgatggcgt ggtgtatgtc tccggtacgc tggcttttga tcaacataat     120
aacgtgctgt ttgccgatga cccaaaggcg caaacccgcc acgttctgga aactatccgc     180
aaggtgatcg agacggcggg tggcacgatg gcggatgtga ccttcaacag catctttatt     240
accgactgga aaattacgcg cgcgattaac gaaatctacg ccgagttttt tccgggtgat     300
aaaccggcgc gattctgcat tcagtgcgga ctggtaaaac ctgacgcgct ggtggaaatc     360
gccacaattg cgcatatcgc caagtga                                         387
```

<210> SEQ ID NO 6
<211> LENGTH: 128
<212> TYPE: PRT
<213> ORGANISM: Escherichia coli

<400> SEQUENCE: 6

Met Pro Lys Ser Val Ile Ile Pro Ala Gly Ser Ser Ala Pro Leu Ala
1               5                   10                  15

Pro Phe Val Pro Gly Thr Leu Ala Asp Gly Val Val Tyr Val Ser Gly
            20                  25                  30

Thr Leu Ala Phe Asp Gln His Asn Asn Val Leu Phe Ala Asp Asp Pro
        35                  40                  45

Lys Ala Gln Thr Arg His Val Leu Glu Thr Ile Arg Lys Val Ile Glu
    50                  55                  60

Thr Ala Gly Gly Thr Met Ala Asp Val Thr Phe Asn Ser Ile Phe Ile
65                  70                  75                  80

Thr Asp Trp Lys Asn Tyr Ala Ala Ile Asn Glu Ile Tyr Ala Glu Phe
                85                  90                  95

Phe Pro Gly Asp Lys Pro Ala Arg Phe Cys Ile Gln Cys Gly Leu Val
            100                 105                 110

Lys Pro Asp Ala Leu Val Glu Ile Ala Thr Ile Ala His Ile Ala Lys
        115                 120                 125

<210> SEQ ID NO 7
<211> LENGTH: 390
<212> TYPE: DNA
<213> ORGANISM: Escherichia coli

<400> SEQUENCE: 7

```
atgaaaaaga ttatcgaaac gcaacgtgcc ccaggcgcaa tcggcccctta tgttcagggc      60
gttgatttag gcagcatggt cttcacctcc ggcaaatac cggtttgccc acagaccggt     120
gagatcccgg ctgatgtgca agatcaggcg cgtttaagcc tcgaaaacgt caaagcgatc     180
gtggttgctg ccgggctgag cgtgggcgat atcatcaaga tgaccgtgtt ataccgat       240
ctgaatgatt ttgccaccat caacgaagtc tataagcagt tcttcgatga gcatcaggcg     300
acctatccga cccggagctg tgtgcaggtc gcgcgtttgc cgaaagatgt gaagctggaa     360
attgaagcca tcgcagtacg tagtgcgtaa                                      390
```

<210> SEQ ID NO 8
<211> LENGTH: 129
<212> TYPE: PRT
<213> ORGANISM: Escherichia coli

<400> SEQUENCE: 8

Met Lys Lys Ile Ile Glu Thr Gln Arg Ala Pro Gly Ala Ile Gly Pro
1               5                   10                  15

Tyr Val Gln Gly Val Asp Leu Gly Ser Met Val Phe Thr Ser Gly Gln
            20                  25                  30

Ile Pro Val Cys Pro Gln Thr Gly Glu Ile Pro Ala Asp Val Gln Asp
        35                  40                  45

Gln Ala Arg Leu Ser Leu Glu Asn Val Lys Ala Ile Val Ala Ala
    50                  55                  60

Gly Leu Ser Val Gly Asp Ile Ile Lys Met Thr Val Phe Ile Thr Asp
65                  70                  75                  80

Leu Asn Asp Phe Ala Thr Ile Asn Glu Val Tyr Lys Gln Phe Phe Asp
                85                  90                  95

Glu His Gln Ala Thr Tyr Pro Thr Arg Ser Cys Val Gln Val Ala Arg
            100                 105                 110

Leu Pro Lys Asp Val Lys Leu Glu Ile Glu Ala Ile Ala Val Arg Ser
            115                 120                 125

Ala

<210> SEQ ID NO 9
<211> LENGTH: 345
<212> TYPE: DNA
<213> ORGANISM: Escherichia coli

<400> SEQUENCE: 9
atgactatcg ttcgtatcga tgctgaagcc cgctggtctg atgtagtaat ccacaacaac      60
acgctctact acactggtgt accggaaaac ctcgacgccg atgcctttga gcaaccgcc     120 aacacgctgg cacagattga cgccgtgctg aaaaacagg gcagcaataa atcgagcatt     180
ctggatgcca ccatttttcct ggccgataaa aacgacttcg cggcgatgaa taaagcgtgg     240
gatgcttggg ttgtcgcggg tcatgcgccg gtgcgctgca cggtacaagc gggttttgatg     300 aacccgaagt ataaagttga aattaagatt gtggctgcgg tgtaa                     345

<210> SEQ ID NO 10
<211> LENGTH: 114
<212> TYPE: PRT
<213> ORGANISM: Escherichia coli

<400> SEQUENCE: 10

Met Thr Ile Val Arg Ile Asp Ala Glu Ala Arg Trp Ser Asp Val Val
1               5                   10                  15

Ile His Asn Asn Thr Leu Tyr Tyr Thr Gly Val Pro Glu Asn Leu Asp
            20                  25                  30

Ala Asp Ala Phe Glu Gln Thr Ala Asn Thr Leu Ala Gln Ile Asp Ala
        35                  40                  45

Val Leu Glu Lys Gln Gly Ser Asn Lys Ser Ser Ile Leu Asp Ala Thr
    50                  55                  60

Ile Phe Leu Ala Asp Lys Asn Asp Phe Ala Ala Met Asn Lys Ala Trp
65                  70                  75                  80

Asp Ala Trp Val Val Ala Gly His Ala Pro Val Arg Cys Thr Val Gln
                85                  90                  95

Ala Gly Leu Met Asn Pro Lys Tyr Lys Val Glu Ile Lys Ile Val Ala
            100                 105                 110

Ala Val

<210> SEQ ID NO 11
<211> LENGTH: 396
<212> TYPE: DNA
<213> ORGANISM: Escherichia coli

<400> SEQUENCE: 11
atggtagaaa gaaccgctgt tttccctgct ggccgacatt cactatatgc tgagcatcgt     60
tattctgcgg ctattcgttc cggcgatttg ctgtttgttt ccgggcaagt aggaagtcga    120
gaggacggaa caccagaacc cgattttcag caacaagtca gactggcatt tgataatttg    180
catgcgaccc tggcagctgc gggatgcact tttgacgata tcattgatgt tacgagcttc    240
cataccgatc cagaaaacca atttgaagac atcatgacgg tgaaaaatga aatatttagc    300
gccccacctt atccaaactg gacggcggtg ggtgttacat ggctggcagg ctttgatttt    360
gaaattaaag tgatagcgcg catccctgag cagtaa                              396

<210> SEQ ID NO 12
<211> LENGTH: 131
<212> TYPE: PRT
<213> ORGANISM: Escherichia coli

<400> SEQUENCE: 12

Met Val Glu Arg Thr Ala Val Phe Pro Ala Gly Arg His Ser Leu Tyr
1               5                   10                  15

Ala Glu His Arg Tyr Ser Ala Ala Ile Arg Ser Gly Asp Leu Leu Phe
            20                  25                  30

Val Ser Gly Gln Val Gly Ser Arg Glu Asp Gly Thr Pro Glu Pro Asp
        35                  40                  45

Phe Gln Gln Gln Val Arg Leu Ala Phe Asp Asn Leu His Ala Thr Leu
    50                  55                  60

Ala Ala Ala Gly Cys Thr Phe Asp Asp Ile Ile Asp Val Thr Ser Phe
65                  70                  75                  80

His Thr Asp Pro Glu Asn Gln Phe Glu Asp Ile Met Thr Val Lys Asn
                85                  90                  95

Glu Ile Phe Ser Ala Pro Pro Tyr Pro Asn Trp Thr Ala Val Gly Val
            100                 105                 110

Thr Trp Leu Ala Gly Phe Asp Phe Glu Ile Lys Val Ile Ala Arg Ile
        115                 120                 125

Pro Glu Gln
    130

<210> SEQ ID NO 13
<211> LENGTH: 449
<212> TYPE: PRT
<213> ORGANISM: Escherichia coli

<400> SEQUENCE: 13

Met Ser Glu Ile Val Val Ser Lys Phe Gly Gly Thr Ser Val Ala Asp
1               5                   10                  15

Phe Asp Ala Met Asn Arg Ser Ala Asp Ile Val Leu Ser Asp Ala Asn
            20                  25                  30

Val Arg Leu Val Val Leu Ser Ala Ser Ala Gly Ile Thr Asn Leu Leu
        35                  40                  45

```
Val Ala Leu Ala Glu Gly Leu Glu Pro Gly Glu Arg Phe Glu Lys Leu
            50              55              60
Asp Ala Ile Arg Asn Ile Gln Phe Ala Ile Leu Glu Arg Leu Arg Tyr
65              70              75              80
Pro Asn Val Ile Arg Glu Ile Glu Arg Leu Leu Glu Asn Ile Thr
                85              90              95
Val Leu Ala Glu Ala Ala Leu Ala Thr Ser Pro Ala Leu Thr Asp
            100             105             110
Glu Leu Val Ser His Gly Leu Met Ser Thr Leu Leu Phe Val Glu
            115             120             125
Ile Leu Arg Glu Arg Asp Val Gln Ala Gln Trp Phe Asp Val Arg Lys
        130             135             140
Val Met Arg Thr Asn Asp Arg Phe Gly Arg Ala Glu Pro Asp Ile Ala
145             150             155             160
Ala Leu Ala Glu Leu Ala Ala Leu Gln Leu Leu Pro Arg Leu Asn Glu
            165             170             175
Gly Leu Val Ile Thr Gln Gly Phe Ile Gly Ser Glu Asn Lys Gly Arg
            180             185             190
Thr Thr Thr Leu Gly Arg Gly Gly Ser Asp Tyr Thr Ala Ala Leu Leu
        195             200             205
Ala Glu Ala Leu His Ala Ser Arg Val Asp Ile Trp Thr Asp Val Pro
210             215             220
Gly Ile Tyr Thr Thr Asp Pro Arg Val Val Ser Ala Ala Lys Arg Ile
225             230             235             240
Asp Glu Ile Ala Phe Ala Glu Ala Ala Glu Met Ala Thr Phe Gly Ala
            245             250             255
Lys Val Leu His Pro Ala Thr Leu Leu Pro Ala Val Arg Ser Asp Ile
            260             265             270
Pro Val Phe Val Gly Ser Ser Lys Asp Pro Arg Ala Gly Gly Thr Leu
        275             280             285
Val Cys Asn Lys Thr Glu Asn Pro Pro Leu Phe Arg Ala Leu Ala Leu
290             295             300
Arg Arg Asn Gln Thr Leu Leu Thr Leu His Ser Leu Asn Met Leu His
305             310             315             320
Ser Arg Gly Phe Leu Ala Glu Val Phe Gly Ile Leu Ala Arg His Asn
            325             330             335
Ile Ser Val Asp Leu Ile Thr Thr Ser Glu Val Ser Val Ala Leu Thr
            340             345             350
Leu Asp Thr Thr Gly Ser Thr Ser Thr Gly Asp Thr Leu Leu Thr Gln
        355             360             365
Ser Leu Leu Met Glu Leu Ser Ala Leu Cys Arg Val Glu Val Glu Glu
        370             375             380
Gly Leu Ala Leu Val Ala Leu Ile Gly Asn Asp Leu Ser Lys Ala Cys
385             390             395             400
Gly Val Gly Lys Glu Val Phe Gly Val Leu Glu Pro Phe Asn Ile Arg
            405             410             415
Met Ile Cys Tyr Gly Ala Ser Ser His Asn Leu Cys Phe Leu Val Pro
            420             425             430
Gly Glu Asp Ala Glu Gln Val Val Gln Lys Leu His Ser Asn Leu Phe
        435             440             445
Glu
```

-continued

<210> SEQ ID NO 14
<211> LENGTH: 292
<212> TYPE: PRT
<213> ORGANISM: Escherichia coli

<400> SEQUENCE: 14

Met Phe Thr Gly Ser Ile Val Ala Ile Val Thr Pro Met Asp Glu Lys
1               5                   10                  15

Gly Asn Val Cys Arg Ala Ser Leu Lys Lys Leu Ile Asp Tyr His Val
            20                  25                  30

Ala Ser Gly Thr Ser Ala Ile Val Ser Val Gly Thr Thr Gly Glu Ser
        35                  40                  45

Ala Thr Leu Asn His Asp Glu His Ala Asp Val Val Met Met Thr Leu
    50                  55                  60

Asp Leu Ala Asp Gly Arg Ile Pro Val Ile Ala Gly Thr Gly Ala Asn
65                  70                  75                  80

Ala Thr Ala Glu Ala Ile Ser Leu Thr Gln Arg Phe Asn Asp Ser Gly
                85                  90                  95

Ile Val Gly Cys Leu Thr Val Thr Pro Tyr Tyr Asn Arg Pro Ser Gln
            100                 105                 110

Glu Gly Leu Tyr Gln His Phe Lys Ala Ile Ala Glu His Thr Asp Leu
        115                 120                 125

Pro Gln Ile Leu Tyr Asn Val Pro Ser Arg Thr Gly Cys Asp Leu Leu
    130                 135                 140

Pro Glu Thr Val Gly Arg Leu Ala Lys Val Lys Asn Ile Ile Gly Ile
145                 150                 155                 160

Lys Glu Ala Thr Gly Asn Leu Thr Arg Val Asn Gln Ile Lys Glu Leu
                165                 170                 175

Val Ser Asp Asp Phe Val Leu Leu Ser Gly Asp Asp Ala Ser Ala Leu
            180                 185                 190

Asp Phe Met Gln Leu Gly Gly His Gly Val Ile Ser Val Thr Ala Asn
        195                 200                 205

Val Ala Ala Arg Asp Met Ala Gln Met Cys Lys Leu Ala Ala Glu Gly
    210                 215                 220

His Phe Ala Glu Ala Arg Val Ile Asn Gln Arg Leu Met Pro Leu His
225                 230                 235                 240

Asn Lys Leu Phe Val Glu Pro Asn Pro Ile Pro Val Lys Trp Ala Cys
                245                 250                 255

Lys Glu Leu Gly Leu Val Ala Thr Asp Thr Leu Arg Leu Pro Met Thr
            260                 265                 270

Pro Ile Thr Asp Ser Gly Arg Glu Thr Val Arg Ala Ala Leu Lys His
        275                 280                 285

Ala Gly Leu Leu
    290

<210> SEQ ID NO 15
<211> LENGTH: 420
<212> TYPE: PRT
<213> ORGANISM: Escherichia coli

<400> SEQUENCE: 15

Met Pro His Ser Leu Phe Ser Thr Asp Thr Asp Leu Thr Ala Glu Asn
1               5                   10                  15

Leu Leu Arg Leu Pro Ala Glu Phe Gly Cys Pro Val Trp Val Tyr Asp
            20                  25                  30

Ala Gln Ile Ile Arg Arg Gln Ile Ala Ala Leu Lys Gln Phe Asp Val

```
            35                  40                  45
Val Arg Phe Ala Gln Lys Ala Cys Ser Asn Ile His Ile Leu Arg Leu
 50                  55                  60

Met Arg Glu Gln Gly Val Lys Val Asp Ser Val Ser Leu Gly Glu Ile
 65                  70                  75                  80

Glu Arg Ala Leu Ala Ala Gly Tyr Asn Pro Gln Thr His Pro Asp Asp
                 85                  90                  95

Ile Val Phe Thr Ala Asp Val Ile Asp Gln Ala Thr Leu Glu Arg Val
                100                 105                 110

Ser Glu Leu Gln Ile Pro Val Asn Ala Gly Ser Val Asp Met Leu Asp
                115                 120                 125

Gln Leu Gly Gln Val Ser Pro Gly His Arg Val Trp Leu Arg Val Asn
130                 135                 140

Pro Gly Phe Gly His Gly His Ser Gln Lys Thr Asn Thr Gly Gly Glu
145                 150                 155                 160

Asn Ser Lys His Gly Ile Trp Tyr Thr Asp Leu Pro Ala Ala Leu Asp
                165                 170                 175

Val Ile Gln Arg His His Leu Gln Leu Val Gly Ile His Met His Ile
                180                 185                 190

Gly Ser Gly Val Asp Tyr Ala His Leu Glu Gln Val Cys Gly Ala Met
                195                 200                 205

Val Arg Gln Val Ile Glu Phe Gly Gln Asp Leu Gln Ala Ile Ser Ala
210                 215                 220

Gly Gly Gly Leu Ser Val Pro Tyr Gln Gly Glu Glu Ala Val Asp
225                 230                 235                 240

Thr Glu His Tyr Tyr Gly Leu Trp Asn Ala Ala Arg Glu Gln Ile Ala
                245                 250                 255

Arg His Leu Gly His Pro Val Lys Leu Glu Ile Glu Pro Gly Arg Phe
                260                 265                 270

Leu Val Ala Gln Ser Gly Val Leu Ile Thr Gln Val Arg Ser Val Lys
                275                 280                 285

Gln Met Gly Ser Arg His Phe Val Leu Val Asp Ala Gly Phe Asn Asp
290                 295                 300

Leu Met Arg Pro Ala Met Tyr Gly Ser Tyr His His Ile Ser Ala Leu
305                 310                 315                 320

Ala Ala Asp Gly Arg Ser Leu Glu His Ala Pro Thr Val Glu Thr Val
                325                 330                 335

Val Ala Gly Pro Leu Cys Glu Ser Gly Asp Val Phe Thr Gln Gln Glu
                340                 345                 350

Gly Gly Asn Val Glu Thr Arg Ala Leu Pro Glu Val Lys Ala Gly Asp
                355                 360                 365

Tyr Leu Val Leu His Asp Thr Gly Ala Tyr Gly Ala Ser Met Ser Ser
                370                 375                 380

Asn Tyr Asn Ser Arg Pro Leu Leu Pro Glu Val Leu Phe Asp Asn Gly
385                 390                 395                 400

Gln Ala Arg Leu Ile Arg Arg Gln Thr Ile Glu Glu Leu Leu Ala
                405                 410                 415

Leu Glu Leu Leu
            420

<210> SEQ ID NO 16
<211> LENGTH: 449
<212> TYPE: PRT
<213> ORGANISM: Artificial Sequence
```

<220> FEATURE:
<223> OTHER INFORMATION: LysC-1 M318I, G323D polypeptide sequence

<400> SEQUENCE: 16

| | | | | | | | | | | | | | | |
|---|---|---|---|---|---|---|---|---|---|---|---|---|---|---|
| Met | Ser | Glu | Ile | Val | Val | Ser | Lys | Phe | Gly | Gly | Thr | Ser | Val | Ala | Asp |
| 1 | | | | 5 | | | | | 10 | | | | | 15 | |

Phe Asp Ala Met Asn Arg Ser Ala Asp Ile Val Leu Ser Asp Ala Asn
                20                  25                  30

Val Arg Leu Val Val Leu Ser Ala Ser Ala Gly Ile Thr Asn Leu Leu
            35                  40                  45

Val Ala Leu Ala Glu Gly Leu Glu Pro Gly Glu Arg Phe Glu Lys Leu
50                  55                  60

Asp Ala Ile Arg Asn Ile Gln Phe Ala Ile Leu Glu Arg Leu Arg Tyr
65                  70                  75                  80

Pro Asn Val Ile Arg Glu Glu Ile Glu Arg Leu Leu Glu Asn Ile Thr
                85                  90                  95

Val Leu Ala Glu Ala Ala Leu Ala Thr Ser Pro Ala Leu Thr Asp
            100                 105                 110

Glu Leu Val Ser His Gly Glu Leu Met Ser Thr Leu Leu Phe Val Glu
        115                 120                 125

Ile Leu Arg Glu Arg Asp Val Gln Ala Gln Trp Phe Asp Val Arg Lys
130                 135                 140

Val Met Arg Thr Asn Asp Arg Phe Gly Arg Ala Glu Pro Asp Ile Ala
145                 150                 155                 160

Ala Leu Ala Glu Leu Ala Ala Leu Gln Leu Leu Pro Arg Leu Asn Glu
                165                 170                 175

Gly Leu Val Ile Thr Gln Gly Phe Ile Gly Ser Glu Asn Lys Gly Arg
            180                 185                 190

Thr Thr Thr Leu Gly Arg Gly Gly Ser Asp Tyr Thr Ala Ala Leu Leu
        195                 200                 205

Ala Glu Ala Leu His Ala Ser Arg Val Asp Ile Trp Thr Asp Val Pro
210                 215                 220

Gly Ile Tyr Thr Thr Asp Pro Arg Val Val Ser Ala Ala Lys Arg Ile
225                 230                 235                 240

Asp Glu Ile Ala Phe Ala Glu Ala Ala Glu Met Ala Thr Phe Gly Ala
                245                 250                 255

Lys Val Leu His Pro Ala Thr Leu Leu Pro Ala Val Arg Ser Asp Ile
            260                 265                 270

Pro Val Phe Val Gly Ser Ser Lys Asp Pro Arg Ala Gly Gly Thr Leu
        275                 280                 285

Val Cys Asn Lys Thr Glu Asn Pro Pro Leu Phe Arg Ala Leu Ala Leu
290                 295                 300

Arg Arg Asn Gln Thr Leu Leu Thr Leu His Ser Leu Asn Ile Leu His
305                 310                 315                 320

Ser Arg Asp Phe Leu Ala Glu Val Phe Gly Ile Leu Ala Arg His Asn
                325                 330                 335

Ile Ser Val Asp Leu Ile Thr Thr Ser Glu Val Ser Val Ala Leu Thr
            340                 345                 350

Leu Asp Thr Thr Gly Ser Thr Ser Thr Gly Asp Thr Leu Leu Thr Gln
        355                 360                 365

Ser Leu Leu Met Glu Leu Ser Ala Leu Cys Arg Val Glu Val Glu Glu
370                 375                 380

Gly Leu Ala Leu Val Ala Leu Ile Gly Asn Asp Leu Ser Lys Ala Cys
385                 390                 395                 400

-continued

```
Gly Val Gly Lys Glu Val Phe Gly Val Leu Glu Pro Phe Asn Ile Arg
                405                 410                 415
Met Ile Cys Tyr Gly Ala Ser Ser His Asn Leu Cys Phe Leu Val Pro
            420                 425                 430
Gly Glu Asp Ala Glu Gln Val Val Gln Lys Leu His Ser Asn Leu Phe
        435                 440                 445
Glu

<210> SEQ ID NO 17
<211> LENGTH: 425
<212> TYPE: PRT
<213> ORGANISM: Artificial Sequence
<220> FEATURE:
<223> OTHER INFORMATION: S-LysC polypeptide sequence

<400> SEQUENCE: 17

Met Gly Leu Val Val Gln Lys Tyr Gly Gly Ser Ser Val Ala Asp Ala
1               5                   10                  15
Glu Gly Ile Lys Arg Val Ala Lys Arg Ile Val Glu Ala Lys Lys Asn
            20                  25                  30
Gly Asn Gln Val Ala Val Val Ser Ala Met Gly Asp Thr Thr Asp
        35                  40                  45
Glu Leu Ile Asp Leu Ala Glu Gln Val Ser Pro Ile Pro Ala Gly Arg
50                  55                  60
Glu Leu Asp Met Leu Leu Thr Ala Gly Glu Arg Ile Ser Met Ala Leu
65                  70                  75                  80
Leu Ala Met Ala Ile Lys Asn Leu Gly His Glu Ala Gln Ser Phe Thr
                85                  90                  95
Gly Ser Gln Ala Gly Val Ile Thr Asp Ser Val His Asn Lys Ala Arg
            100                 105                 110
Ile Ile Asp Val Thr Pro Gly Arg Ile Arg Thr Ser Val Asp Glu Gly
        115                 120                 125
Asn Val Ala Ile Val Ala Gly Phe Gln Gly Val Ser Gln Asp Ser Lys
130                 135                 140
Asp Ile Thr Thr Leu Gly Arg Gly Gly Ser Asp Thr Thr Ala Val Ala
145                 150                 155                 160
Leu Ala Ala Ala Leu Asp Ala Asp Val Cys Glu Ile Tyr Thr Asp Val
                165                 170                 175
Asp Gly Val Phe Thr Ala Asp Pro Arg Val Val Pro Lys Ala Lys Lys
            180                 185                 190
Ile Asp Trp Ile Ser Phe Glu Asp Met Leu Glu Leu Ala Ala Ser Gly
        195                 200                 205
Ser Lys Val Leu Leu His Arg Cys Val Glu Tyr Ala Arg Arg Tyr Asn
210                 215                 220
Ile Pro Ile His Val Arg Ser Ser Phe Ser Gly Leu Gln Gly Thr Trp
225                 230                 235                 240
Val Ser Ser Glu Pro Ile Lys Gln Gly Glu Lys His Val Glu Gln Ala
                245                 250                 255
Leu Ile Ser Gly Val Ala His Asp Thr Ser Glu Ala Lys Val Thr Val
            260                 265                 270
Val Gly Val Pro Asp Lys Pro Gly Glu Ala Ala Ile Phe Arg Ala
        275                 280                 285
Ile Ala Asp Ala Gln Val Asn Ile Asp Met Val Val Gln Asn Val Ser
290                 295                 300
```

```
Ala Ala Ser Thr Gly Leu Thr Asp Ile Ser Phe Thr Leu Pro Lys Ser
305                 310                 315                 320

Glu Gly Arg Lys Ala Ile Asp Ala Leu Glu Lys Asn Arg Pro Gly Ile
            325                 330                 335

Gly Phe Asp Ser Leu Arg Tyr Asp Asp Gln Ile Gly Lys Ile Ser Leu
            340                 345                 350

Val Gly Ala Gly Met Lys Ser Asn Pro Gly Val Thr Ala Asp Phe Phe
            355                 360                 365

Thr Ala Leu Ser Asp Ala Gly Val Asn Ile Glu Leu Ile Ser Thr Ser
            370                 375                 380

Glu Ile Arg Ile Ser Val Val Thr Arg Lys Asp Asp Val Asn Glu Ala
385                 390                 395                 400

Val Arg Ala Val His Thr Ala Phe Gly Leu Asp Ser Asp Ser Asp Glu
            405                 410                 415

Ala Val Val Tyr Gly Gly Thr Gly Arg
            420                 425

<210> SEQ ID NO 18
<211> LENGTH: 350
<212> TYPE: PRT
<213> ORGANISM: Escherichia coli

<400> SEQUENCE: 18

Met Lys Asn Val Gly Phe Ile Gly Trp Arg Gly Met Val Gly Ser Val
1               5                   10                  15

Leu Met Gln Arg Met Val Glu Glu Arg Asp Phe Asp Ala Ile Arg Pro
            20                  25                  30

Val Phe Phe Ser Thr Ser Gln Leu Gly Gln Ala Ala Pro Ser Phe Gly
        35                  40                  45

Gly Thr Thr Gly Thr Leu Gln Asp Ala Phe Asp Leu Glu Ala Leu Lys
    50                  55                  60

Ala Leu Asp Ile Ile Val Thr Cys Gln Gly Gly Asp Tyr Thr Asn Glu
65                  70                  75                  80

Ile Tyr Pro Lys Leu Arg Glu Ser Gly Trp Gln Gly Tyr Trp Ile Asp
                85                  90                  95

Ala Ala Ser Ser Leu Arg Met Lys Asp Asp Ala Ile Ile Ile Leu Asp
            100                 105                 110

Pro Val Asn Gln Asp Val Ile Thr Asp Gly Leu Asn Asn Gly Ile Arg
        115                 120                 125

Thr Phe Val Gly Gly Asn Cys Thr Val Ser Leu Met Leu Met Ser Leu
    130                 135                 140

Gly Gly Leu Phe Ala Asn Asp Leu Val Asp Trp Val Ser Val Ala Thr
145                 150                 155                 160

Tyr Gln Ala Ala Ser Gly Gly Gly Ala Arg His Met Arg Glu Leu Leu
                165                 170                 175

Thr Gln Met Gly His Leu Tyr Gly His Val Ala Asp Glu Leu Ala Thr
            180                 185                 190

Pro Ser Ser Ala Ile Leu Asp Ile Glu Arg Lys Val Thr Thr Leu Thr
        195                 200                 205

Arg Ser Gly Glu Leu Pro Val Asp Asn Phe Gly Val Pro Leu Ala Gly
    210                 215                 220

Ser Leu Ile Pro Trp Ile Asp Lys Gln Leu Asp Asn Gly Gln Ser Arg
225                 230                 235                 240

Glu Glu Trp Lys Gly Gln Ala Glu Thr Asn Lys Ile Leu Asn Thr Ser
                245                 250                 255
```

```
Ser Val Ile Pro Val Asp Gly Leu Cys Val Arg Val Gly Ala Leu Arg
            260                 265                 270

Cys His Ser Gln Ala Phe Thr Ile Lys Leu Lys Lys Asp Val Ser Ile
        275                 280                 285

Pro Thr Val Glu Glu Leu Leu Ala Ala His Asn Pro Trp Ala Lys Val
    290                 295                 300

Val Pro Asn Asp Arg Glu Ile Thr Met Arg Glu Leu Thr Pro Ala Ala
305                 310                 315                 320

Val Thr Gly Thr Leu Thr Thr Pro Val Gly Arg Leu Arg Lys Leu Asn
                325                 330                 335

Met Gly Pro Glu Phe Leu Ser Ala Phe Thr Val Gly Asp Gln
            340                 345                 350

<210> SEQ ID NO 19
<211> LENGTH: 273
<212> TYPE: PRT
<213> ORGANISM: Escherichia coli

<400> SEQUENCE: 19

Met His Asp Ala Asn Ile Arg Val Ala Ile Ala Gly Ala Gly Gly Arg
1               5                   10                  15

Met Gly Arg Gln Leu Ile Gln Ala Ala Leu Ala Leu Glu Gly Val Gln
            20                  25                  30

Leu Gly Ala Ala Leu Glu Arg Glu Gly Ser Ser Leu Leu Gly Ser Asp
        35                  40                  45

Ala Gly Glu Leu Ala Gly Ala Gly Lys Thr Gly Val Thr Val Gln Ser
    50                  55                  60

Ser Leu Asp Ala Val Lys Asp Asp Phe Asp Val Phe Ile Asp Phe Thr
65                  70                  75                  80

Arg Pro Glu Gly Thr Leu Asn His Leu Ala Phe Cys Arg Gln His Gly
                85                  90                  95

Lys Gly Met Val Ile Gly Thr Thr Gly Phe Asp Glu Ala Gly Lys Gln
            100                 105                 110

Ala Ile Arg Asp Ala Ala Ala Asp Ile Ala Ile Val Phe Ala Ala Asn
        115                 120                 125

Phe Ser Val Gly Val Asn Val Met Leu Lys Leu Leu Glu Lys Ala Ala
    130                 135                 140

Lys Val Met Gly Asp Tyr Thr Asp Ile Glu Ile Ile Glu Ala His His
145                 150                 155                 160

Arg His Lys Val Asp Ala Pro Ser Gly Thr Ala Leu Ala Met Gly Glu
                165                 170                 175

Ala Ile Ala His Ala Leu Asp Lys Asp Leu Lys Asp Cys Ala Val Tyr
            180                 185                 190

Ser Arg Glu Gly His Thr Gly Glu Arg Val Pro Gly Thr Ile Gly Phe
        195                 200                 205

Ala Thr Val Arg Ala Gly Asp Ile Val Gly Glu His Thr Ala Met Phe
    210                 215                 220

Ala Asp Ile Gly Glu Arg Leu Glu Ile Thr His Lys Ala Ser Ser Arg
225                 230                 235                 240

Met Thr Phe Ala Asn Gly Ala Val Arg Ser Ala Leu Trp Leu Ser Gly
                245                 250                 255

Lys Glu Ser Gly Leu Phe Asp Met Arg Asp Val Leu Asp Leu Asn Asn
            260                 265                 270

Leu
```

```
<210> SEQ ID NO 20
<211> LENGTH: 274
<212> TYPE: PRT
<213> ORGANISM: Escherichia coli

<400> SEQUENCE: 20

Met Gln Gln Leu Gln Asn Ile Ile Glu Thr Ala Phe Glu Arg Arg Ala
1               5                   10                  15

Glu Ile Thr Pro Ala Asn Ala Asp Thr Val Thr Arg Glu Ala Val Asn
            20                  25                  30

Gln Val Ile Ala Leu Leu Asp Ser Gly Ala Leu Arg Val Ala Glu Lys
        35                  40                  45

Ile Asp Gly Gln Trp Val Thr His Gln Trp Leu Lys Lys Ala Val Leu
    50                  55                  60

Leu Ser Phe Arg Ile Asn Asp Asn Gln Val Ile Glu Gly Ala Glu Ser
65                  70                  75                  80

Arg Tyr Phe Asp Lys Val Pro Met Lys Phe Ala Asp Tyr Asp Glu Ala
                85                  90                  95

Arg Phe Gln Lys Glu Gly Phe Arg Val Val Pro Ala Ala Val Arg
            100                 105                 110

Gln Gly Ala Phe Ile Ala Arg Asn Thr Val Leu Met Pro Ser Tyr Val
        115                 120                 125

Asn Ile Gly Ala Tyr Val Asp Glu Gly Thr Met Val Asp Thr Trp Ala
    130                 135                 140

Thr Val Gly Ser Cys Ala Gln Ile Gly Lys Asn Val His Leu Ser Gly
145                 150                 155                 160

Gly Val Gly Ile Gly Gly Val Leu Glu Pro Leu Gln Ala Asn Pro Thr
                165                 170                 175

Ile Ile Glu Asp Asn Cys Phe Ile Gly Ala Arg Ser Glu Val Val Glu
            180                 185                 190

Gly Val Ile Val Glu Gly Ser Val Ile Ser Met Gly Val Tyr Ile
        195                 200                 205

Gly Gln Ser Thr Arg Ile Tyr Asp Arg Glu Thr Gly Glu Ile His Tyr
    210                 215                 220

Gly Arg Val Pro Ala Gly Ser Val Val Ser Gly Asn Leu Pro Ser
225                 230                 235                 240

Lys Asp Gly Lys Tyr Ser Leu Tyr Cys Ala Val Ile Val Lys Lys Val
                245                 250                 255

Asp Ala Lys Thr Arg Gly Lys Val Gly Ile Asn Glu Leu Leu Arg Thr
            260                 265                 270

Ile Asp

<210> SEQ ID NO 21
<211> LENGTH: 396
<212> TYPE: PRT
<213> ORGANISM: Escherichia coli

<400> SEQUENCE: 21

Met Phe Glu Asn Ile Thr Ala Ala Pro Ala Asp Pro Ile Leu Gly Leu
1               5                   10                  15

Ala Asp Leu Phe Arg Ala Asp Glu Arg Pro Gly Lys Ile Asn Leu Gly
            20                  25                  30

Ile Gly Val Tyr Lys Asp Glu Thr Gly Lys Thr Pro Val Leu Thr Ser
        35                  40                  45
```

```
Val Lys Lys Ala Glu Gln Tyr Leu Leu Glu Asn Glu Thr Lys Asn
 50                  55                  60

Tyr Leu Gly Ile Asp Gly Ile Pro Glu Phe Gly Arg Cys Thr Gln Glu
 65                  70                  75                  80

Leu Leu Phe Gly Lys Gly Ser Ala Leu Ile Asn Asp Lys Arg Ala Arg
                 85                  90                  95

Thr Ala Gln Thr Pro Gly Gly Thr Gly Ala Leu Arg Val Ala Ala Asp
                100                 105                 110

Phe Leu Ala Lys Asn Thr Ser Val Lys Arg Val Trp Val Ser Asn Pro
                115                 120                 125

Ser Trp Pro Asn His Lys Ser Val Phe Asn Ser Ala Gly Leu Glu Val
130                 135                 140

Arg Glu Tyr Ala Tyr Tyr Asp Ala Glu Asn His Thr Leu Asp Phe Asp
145                 150                 155                 160

Ala Leu Ile Asn Ser Leu Asn Glu Ala Gln Ala Gly Asp Val Val Leu
                165                 170                 175

Phe His Gly Cys Cys His Asn Pro Thr Gly Ile Asp Pro Thr Leu Glu
                180                 185                 190

Gln Trp Gln Thr Leu Ala Gln Leu Ser Val Glu Lys Gly Trp Leu Pro
                195                 200                 205

Leu Phe Asp Phe Ala Tyr Gln Gly Phe Ala Arg Gly Leu Glu Glu Asp
210                 215                 220

Ala Glu Gly Leu Arg Ala Phe Ala Ala Met His Lys Glu Leu Ile Val
225                 230                 235                 240

Ala Ser Ser Tyr Ser Lys Asn Phe Gly Leu Tyr Asn Glu Arg Val Gly
                245                 250                 255

Ala Cys Thr Leu Val Ala Ala Asp Ser Glu Thr Val Asp Arg Ala Phe
                260                 265                 270

Ser Gln Met Lys Ala Ala Ile Arg Ala Asn Tyr Ser Asn Pro Pro Ala
                275                 280                 285

His Gly Ala Ser Val Val Ala Thr Ile Leu Ser Asn Asp Ala Leu Arg
                290                 295                 300

Ala Ile Trp Glu Gln Glu Leu Thr Asp Met Arg Gln Arg Ile Gln Arg
305                 310                 315                 320

Met Arg Gln Leu Phe Val Asn Thr Leu Gln Glu Lys Gly Ala Asn Arg
                325                 330                 335

Asp Phe Ser Phe Ile Ile Lys Gln Asn Gly Met Phe Ser Phe Ser Gly
                340                 345                 350

Leu Thr Lys Glu Gln Val Leu Arg Leu Arg Glu Glu Phe Gly Val Tyr
                355                 360                 365

Ala Val Ala Ser Gly Arg Val Asn Val Ala Gly Met Thr Pro Asp Asn
                370                 375                 380

Met Ala Pro Leu Cys Glu Ala Ile Val Ala Val Leu
385                 390                 395
```

<210> SEQ ID NO 22
<211> LENGTH: 38
<212> TYPE: DNA
<213> ORGANISM: Artificial Sequence
<220> FEATURE:
<223> OTHER INFORMATION: synthetic promoter nucleic acid sequence

<400> SEQUENCE: 22
agtttattct tgacatgtag tgaggggct ggtataat         38

```
<210> SEQ ID NO 23
<211> LENGTH: 50
<212> TYPE: DNA
<213> ORGANISM: Artificial Sequence
<220> FEATURE:
<223> OTHER INFORMATION: Primer cadA-F

<400> SEQUENCE: 23
ggcgagctca cacaggaaac agaccatgaa cgttattgca atattgaatc          50

<210> SEQ ID NO 24
<211> LENGTH: 53
<212> TYPE: DNA
<213> ORGANISM: Artificial Sequence
<220> FEATURE:
<223> OTHER INFORMATION: Primer cadA-R

<400> SEQUENCE: 24
ggcggatccc cacttccctt gtacgagcta attattttt gctttcttct ttc       53

<210> SEQ ID NO 25
<211> LENGTH: 47
<212> TYPE: DNA
<213> ORGANISM: Artificial Sequence
<220> FEATURE:
<223> OTHER INFORMATION: Primer cadA-F2

<400> SEQUENCE: 25
atttcacaca ggaaacagct atgaacgtta ttgcaatatt gaatcac             47

<210> SEQ ID NO 26
<211> LENGTH: 20
<212> TYPE: DNA
<213> ORGANISM: Artificial Sequence
<220> FEATURE:
<223> OTHER INFORMATION: Primer cadA-R2

<400> SEQUENCE: 26
agctgtttcc tgtgtgaaat                                           20

<210> SEQ ID NO 27
<211> LENGTH: 35
<212> TYPE: DNA
<213> ORGANISM: Artificial Sequence
<220> FEATURE:
<223> OTHER INFORMATION: Primer SacI-F

<400> SEQUENCE: 27
ggcgagctcc tcctgtgtga aattgttatc cgctc                          35

<210> SEQ ID NO 28
<211> LENGTH: 34
<212> TYPE: DNA
<213> ORGANISM: Artificial Sequence
<220> FEATURE:
<223> OTHER INFORMATION: Primer SacI-R

<400> SEQUENCE: 28
ggcgagctca tgaacgttat tgcaatattg aatc                           34

<210> SEQ ID NO 29
<211> LENGTH: 30
<212> TYPE: DNA
<213> ORGANISM: Artificial Sequence
<220> FEATURE:
<223> OTHER INFORMATION: Primer ridA-F
```

```
<400> SEQUENCE: 29
ggcgagctca tgagcaaaac tatcgcgacg                                30

<210> SEQ ID NO 30
<211> LENGTH: 29
<212> TYPE: DNA
<213> ORGANISM: Artificial Sequence
<220> FEATURE:
<223> OTHER INFORMATION: Primer ridA-R

<400> SEQUENCE: 30
ggcggatcct tagcgacgaa cagcgatcg                                 29

<210> SEQ ID NO 31
<211> LENGTH: 32
<212> TYPE: DNA
<213> ORGANISM: Artificial Sequence
<220> FEATURE:
<223> OTHER INFORMATION: Primer rutC-F

<400> SEQUENCE: 31
ggcgagctca tgccaaaatc cgtaattatt cc                             32

<210> SEQ ID NO 32
<211> LENGTH: 29
<212> TYPE: DNA
<213> ORGANISM: Artificial Sequence
<220> FEATURE:
<223> OTHER INFORMATION: Primer rutC-R

<400> SEQUENCE: 32
ggcggatcct cacttggcga tatgcgcaa                                 29

<210> SEQ ID NO 33
<211> LENGTH: 34
<212> TYPE: DNA
<213> ORGANISM: Artificial Sequence
<220> FEATURE:
<223> OTHER INFORMATION: Primer tdcF-F

<400> SEQUENCE: 33
ggcgagctca tgaaaaagat tatcgaaacg caac                           34

<210> SEQ ID NO 34
<211> LENGTH: 29
<212> TYPE: DNA
<213> ORGANISM: Artificial Sequence
<220> FEATURE:
<223> OTHER INFORMATION: Primer tdcF-R

<400> SEQUENCE: 34
ggcggatcct tacgcactac gtactgcga                                 29

<210> SEQ ID NO 35
<211> LENGTH: 34
<212> TYPE: DNA
<213> ORGANISM: Artificial Sequence
<220> FEATURE:
<223> OTHER INFORMATION: Primer yoaB-F

<400> SEQUENCE: 35
ggcgagctca tgactatcgt tcgtatcgat gctg                           34

<210> SEQ ID NO 36
<211> LENGTH: 29
```

```
<212> TYPE: DNA
<213> ORGANISM: Artificial Sequence
<220> FEATURE:
<223> OTHER INFORMATION: Primer yoaB-R

<400> SEQUENCE: 36
ggcggatcct tacaccgcag ccacaatct                                   29

<210> SEQ ID NO 37
<211> LENGTH: 33
<212> TYPE: DNA
<213> ORGANISM: Artificial Sequence
<220> FEATURE:
<223> OTHER INFORMATION: Primer yjgH-F

<400> SEQUENCE: 37
ggcgagctca tggtagaaag aaccgctgtt ttc                              33

<210> SEQ ID NO 38
<211> LENGTH: 31
<212> TYPE: DNA
<213> ORGANISM: Artificial Sequence
<220> FEATURE:
<223> OTHER INFORMATION: Primer yjgH-R

<400> SEQUENCE: 38
ggcggatcct attgcttact gctcagggat g                                31

<210> SEQ ID NO 39
<211> LENGTH: 46
<212> TYPE: DNA
<213> ORGANISM: Artificial Sequence
<220> FEATURE:
<223> OTHER INFORMATION: Primer lysC-F

<400> SEQUENCE: 39
ggcgagctca cacaggaaac agaccatgtc tgaaattgtt gtctcc                46

<210> SEQ ID NO 40
<211> LENGTH: 33
<212> TYPE: DNA
<213> ORGANISM: Artificial Sequence
<220> FEATURE:
<223> OTHER INFORMATION: Primer lysC-R

<400> SEQUENCE: 40
ggcggatcct tactcaaaca aattactatg cag                              33

<210> SEQ ID NO 41
<211> LENGTH: 46
<212> TYPE: DNA
<213> ORGANISM: Artificial Sequence
<220> FEATURE:
<223> OTHER INFORMATION: Primer dapA-F

<400> SEQUENCE: 41
ggcggatcca cacaggaaac agaccatgtt cacgggaagt attgtc                46

<210> SEQ ID NO 42
<211> LENGTH: 28
<212> TYPE: DNA
<213> ORGANISM: Artificial Sequence
<220> FEATURE:
<223> OTHER INFORMATION: Primer dapA-R

<400> SEQUENCE: 42
```

```
ggctctagat tacagcaaac cggcatgc                                           28
```

<210> SEQ ID NO 43
<211> LENGTH: 46
<212> TYPE: DNA
<213> ORGANISM: Artificial Sequence
<220> FEATURE:
<223> OTHER INFORMATION: Primer lysA-F

<400> SEQUENCE: 43

```
ggctctagaa cacaggaaac agaccatgcc acattcactg ttcagc                       46
```

<210> SEQ ID NO 44
<211> LENGTH: 30
<212> TYPE: DNA
<213> ORGANISM: Artificial Sequence
<220> FEATURE:
<223> OTHER INFORMATION: Primer lysA-R

<400> SEQUENCE: 44

```
ggcgtcgact taaagcaatt ccagcgccag                                         30
```

<210> SEQ ID NO 45
<211> LENGTH: 23
<212> TYPE: DNA
<213> ORGANISM: Artificial Sequence
<220> FEATURE:
<223> OTHER INFORMATION: Primer 318-F

<400> SEQUENCE: 45

```
cagcctgaat atactgcatt ctc                                                23
```

<210> SEQ ID NO 46
<211> LENGTH: 23
<212> TYPE: DNA
<213> ORGANISM: Artificial Sequence
<220> FEATURE:
<223> OTHER INFORMATION: Primer 318-R

<400> SEQUENCE: 46

```
gagaatgcag tatattcagg ctg                                                23
```

<210> SEQ ID NO 47
<211> LENGTH: 20
<212> TYPE: DNA
<213> ORGANISM: Artificial Sequence
<220> FEATURE:
<223> OTHER INFORMATION: Primer 323-F

<400> SEQUENCE: 47

```
gcattctcgc gatttcctcg                                                    20
```

<210> SEQ ID NO 48
<211> LENGTH: 20
<212> TYPE: DNA
<213> ORGANISM: Artificial Sequence
<220> FEATURE:
<223> OTHER INFORMATION: Primer 323-R

<400> SEQUENCE: 48

```
cgaggaaatc gcgagaatgc                                                    20
```

<210> SEQ ID NO 49
<211> LENGTH: 46
<212> TYPE: DNA
<213> ORGANISM: Artificial Sequence

```
<220> FEATURE:
<223> OTHER INFORMATION: Primer SlysC-F

<400> SEQUENCE: 49
ggcgagctca cacaggaaac agaccatggg cttagttgtg cagaaa            46

<210> SEQ ID NO 50
<211> LENGTH: 30
<212> TYPE: DNA
<213> ORGANISM: Artificial Sequence
<220> FEATURE:
<223> OTHER INFORMATION: Primer SlysC-R

<400> SEQUENCE: 50
ggcggatcct taacgacctg tgccgccata                               30

<210> SEQ ID NO 51
<211> LENGTH: 48
<212> TYPE: DNA
<213> ORGANISM: Artificial Sequence
<220> FEATURE:
<223> OTHER INFORMATION: Primer asd-F

<400> SEQUENCE: 51
ggcgagctca cacaggaaac agaccatgaa aaatgttggt tttatcgg           48

<210> SEQ ID NO 52
<211> LENGTH: 28
<212> TYPE: DNA
<213> ORGANISM: Artificial Sequence
<220> FEATURE:
<223> OTHER INFORMATION: Primer asd-R

<400> SEQUENCE: 52
ggcggatcct tacgccagtt gacgaagc                                 28

<210> SEQ ID NO 53
<211> LENGTH: 39
<212> TYPE: DNA
<213> ORGANISM: Artificial Sequence
<220> FEATURE:
<223> OTHER INFORMATION: Primer dapB-F

<400> SEQUENCE: 53
ggcacacagg aaacagacca tgcatgatgc aaacatccg                     39

<210> SEQ ID NO 54
<211> LENGTH: 38
<212> TYPE: DNA
<213> ORGANISM: Artificial Sequence
<220> FEATURE:
<223> OTHER INFORMATION: Primer dapB-R

<400> SEQUENCE: 54
ggctctagat tacaaattat tgagatcaag tacatctc                      38

<210> SEQ ID NO 55
<211> LENGTH: 45
<212> TYPE: DNA
<213> ORGANISM: Artificial Sequence
<220> FEATURE:
<223> OTHER INFORMATION: Primer dapD-F

<400> SEQUENCE: 55
ggctctagaa cacaggaaac agaccatgca gcagttacag aacat              45
```

<210> SEQ ID NO 56
<211> LENGTH: 29
<212> TYPE: DNA
<213> ORGANISM: Artificial Sequence
<220> FEATURE:
<223> OTHER INFORMATION: Primer dapD-R

<400> SEQUENCE: 56
ggcgcatgct tagtcgatgg tacgcagca                              29

<210> SEQ ID NO 57
<211> LENGTH: 46
<212> TYPE: DNA
<213> ORGANISM: Artificial Sequence
<220> FEATURE:
<223> OTHER INFORMATION: Primer aspC-F

<400> SEQUENCE: 57
ggctctagaa cacaggaaac agaccatgtt tgagaacatt accgcc           46

<210> SEQ ID NO 58
<211> LENGTH: 47
<212> TYPE: DNA
<213> ORGANISM: Artificial Sequence
<220> FEATURE:
<223> OTHER INFORMATION: Primer aspC-R

<400> SEQUENCE: 58
ggcgcatgcg acctcgaggt agtcgactta cagcactgcc acaatcg          47

<210> SEQ ID NO 59
<211> LENGTH: 42
<212> TYPE: DNA
<213> ORGANISM: Artificial Sequence
<220> FEATURE:
<223> OTHER INFORMATION: Primer lysC-rbs2-F

<400> SEQUENCE: 59
atttcacaca ggaaacagct atgtctgaaa ttgttgtctc ca               42

<210> SEQ ID NO 60
<211> LENGTH: 20
<212> TYPE: DNA
<213> ORGANISM: Artificial Sequence
<220> FEATURE:
<223> OTHER INFORMATION: Primer lysC-rbs2-R

<400> SEQUENCE: 60
agctgtttcc tgtgtgaaat                                        20

<210> SEQ ID NO 61
<211> LENGTH: 46
<212> TYPE: DNA
<213> ORGANISM: Artificial Sequence
<220> FEATURE:
<223> OTHER INFORMATION: Primer asd-rbs2-F

<400> SEQUENCE: 61
atttcacaca ggaaacagct atgaaaaatg ttggttttat cggctg           46

<210> SEQ ID NO 62
<211> LENGTH: 20
<212> TYPE: DNA
<213> ORGANISM: Artificial Sequence
<220> FEATURE:
<223> OTHER INFORMATION: Primer asd-rbs2-R

```
<400> SEQUENCE: 62
agctgtttcc tgtgtgaaat                                               20

<210> SEQ ID NO 63
<211> LENGTH: 29
<212> TYPE: DNA
<213> ORGANISM: Artificial Sequence
<220> FEATURE:
<223> OTHER INFORMATION: Primer SacI-F2

<400> SEQUENCE: 63
ggcgagctct cccctgattc tgtggataa                                     29

<210> SEQ ID NO 64
<211> LENGTH: 29
<212> TYPE: DNA
<213> ORGANISM: Artificial Sequence
<220> FEATURE:
<223> OTHER INFORMATION: Primer SacI-R2

<400> SEQUENCE: 64
ggcgagctca gcaaaaggcc aggaaccgt                                     29

<210> SEQ ID NO 65
<211> LENGTH: 30
<212> TYPE: DNA
<213> ORGANISM: Artificial Sequence
<220> FEATURE:
<223> OTHER INFORMATION: Primer ApaI-F

<400> SEQUENCE: 65
ggcgggcccg tattaccgcc tttgagtgag                                    30

<210> SEQ ID NO 66
<211> LENGTH: 29
<212> TYPE: DNA
<213> ORGANISM: Artificial Sequence
<220> FEATURE:
<223> OTHER INFORMATION: Primer ApaI-R

<400> SEQUENCE: 66
ggcgggccca cagaatcagg ggagagctc                                     29

<210> SEQ ID NO 67
<211> LENGTH: 29
<212> TYPE: DNA
<213> ORGANISM: Artificial Sequence
<220> FEATURE:
<223> OTHER INFORMATION: Primer LAL2-SacI-F

<400> SEQUENCE: 67
ggcgagctcg ttggccgatt cattaatgc                                     29

<210> SEQ ID NO 68
<211> LENGTH: 30
<212> TYPE: DNA
<213> ORGANISM: Artificial Sequence
<220> FEATURE:
<223> OTHER INFORMATION: Primer LAL2-ApaI-R

<400> SEQUENCE: 68
ggcgggccct taaagcaatt ccagcgccag                                    30

<210> SEQ ID NO 69
```

<211> LENGTH: 23
<212> TYPE: DNA
<213> ORGANISM: Artificial Sequence
<220> FEATURE:
<223> OTHER INFORMATION: Primer rmvBamHI-F

<400> SEQUENCE: 69
tgcggtgtaa ggttcctcta gag                                            23

<210> SEQ ID NO 70
<211> LENGTH: 23
<212> TYPE: DNA
<213> ORGANISM: Artificial Sequence
<220> FEATURE:
<223> OTHER INFORMATION: Primer rmvBamHI-R

<400> SEQUENCE: 70
ctctagagga accttacacc gca                                            23

<210> SEQ ID NO 71
<211> LENGTH: 22
<212> TYPE: DNA
<213> ORGANISM: Artificial Sequence
<220> FEATURE:
<223> OTHER INFORMATION: Primer rmvSphI-F

<400> SEQUENCE: 71
gacctgcagg cttgcaagct tg                                             22

<210> SEQ ID NO 72
<211> LENGTH: 22
<212> TYPE: DNA
<213> ORGANISM: Artificial Sequence
<220> FEATURE:
<223> OTHER INFORMATION: Primer rmvSphI-R

<400> SEQUENCE: 72
caagcttgca agcctgcagg tc                                             22

<210> SEQ ID NO 73
<211> LENGTH: 47
<212> TYPE: DNA
<213> ORGANISM: Artificial Sequence
<220> FEATURE:
<223> OTHER INFORMATION: Primer yoaB-F2

<400> SEQUENCE: 73
ggcggatccc acacaggagg agctcatgac tatcgttcgt atcgatg                  47

<210> SEQ ID NO 74
<211> LENGTH: 29
<212> TYPE: DNA
<213> ORGANISM: Artificial Sequence
<220> FEATURE:
<223> OTHER INFORMATION: Primer yoaB-R2

<400> SEQUENCE: 74
ggcgcatgct cattcgccat tcaggctgc                                      29

<210> SEQ ID NO 75
<211> LENGTH: 26
<212> TYPE: DNA
<213> ORGANISM: Artificial Sequence
<220> FEATURE:
<223> OTHER INFORMATION: Primer rmvSphI-F2

<400> SEQUENCE: 75

```
catttgataa tttacatgcg accctg                                              26
```

<210> SEQ ID NO 76
<211> LENGTH: 26
<212> TYPE: DNA
<213> ORGANISM: Artificial Sequence
<220> FEATURE:
<223> OTHER INFORMATION: Primer rmvSphI-R2

<400> SEQUENCE: 76

```
cagggtcgca tgtaaattat caaatg                                              26
```

<210> SEQ ID NO 77
<211> LENGTH: 46
<212> TYPE: DNA
<213> ORGANISM: Artificial Sequence
<220> FEATURE:
<223> OTHER INFORMATION: Primer yjgH-F2

<400> SEQUENCE: 77

```
ggcggatccc acacaggagg agctcatggt agaaagaacc gctgtt                        46
```

<210> SEQ ID NO 78
<211> LENGTH: 29
<212> TYPE: DNA
<213> ORGANISM: Artificial Sequence
<220> FEATURE:
<223> OTHER INFORMATION: Primer yjgH-R2

<400> SEQUENCE: 78

```
ggcgcatgct attgcttact gctcaggga                                           29
```

<210> SEQ ID NO 79
<211> LENGTH: 66
<212> TYPE: DNA
<213> ORGANISM: Artificial Sequence
<220> FEATURE:
<223> OTHER INFORMATION: Primer psyn-1

<400> SEQUENCE: 79

```
ggcgaattca gtttattctt gacatgtagt gaggggctg gtataatgag ctcggtaccc          60
ggggat                                                                    66
```

<210> SEQ ID NO 80
<211> LENGTH: 34
<212> TYPE: DNA
<213> ORGANISM: Artificial Sequence
<220> FEATURE:
<223> OTHER INFORMATION: Primer psyn-2

<400> SEQUENCE: 80

```
ggcagtactc aaccaagtca ttctgagaat agtg                                     34
```

<210> SEQ ID NO 81
<211> LENGTH: 131
<212> TYPE: PRT
<213> ORGANISM: Escherichia coli

<400> SEQUENCE: 81

```
Met Val Glu Arg Thr Ala Val Phe Pro Ala Gly Arg His Ser Leu Tyr
1               5                   10                  15

Ala Glu His Arg Tyr Ser Ala Ala Ile Arg Ser Gly Asp Leu Leu Phe
            20                  25                  30
```

```
Val Ser Gly Gln Val Gly Ser Arg Glu Asp Gly Thr Pro Glu Pro Asp
     35                  40                  45

Phe Gln Gln Val Arg Leu Ala Phe Asp Asn Leu His Ala Thr Leu
 50                  55                  60

Ala Ala Ala Gly Cys Thr Phe Asp Asp Ile Ile Asp Val Thr Ser Phe
 65                  70                  75                  80

His Thr Asp Pro Glu Asn Gln Phe Glu Asp Ile Met Thr Val Lys Asn
                 85                  90                  95

Glu Ile Phe Ser Ala Pro Pro Tyr Pro Asn Trp Thr Ala Val Gly Val
                100                 105                 110

Thr Trp Leu Ala Gly Phe Asp Phe Glu Ile Lys Val Ile Ala Arg Ile
            115                 120                 125

Pro Glu Gln
    130

<210> SEQ ID NO 82
<211> LENGTH: 124
<212> TYPE: PRT
<213> ORGANISM: Arapidopsis thaliana

<400> SEQUENCE: 82

Gly Pro His Met Ser Thr Glu Lys Ala Pro Ala Ala Leu Gly Pro Tyr
 1               5                  10                  15

Ser Gln Ala Ile Lys Ala Asn Asn Leu Val Phe Leu Ser Gly Val Leu
             20                  25                  30

Gly Leu Ile Pro Glu Thr Gly Lys Phe Val Ser Glu Ser Val Glu Asp
             35                  40                  45

Gln Thr Glu Gln Val Leu Lys Asn Met Gly Glu Ile Leu Lys Ala Ser
 50                  55                  60

Gly Ala Asp Tyr Ser Ser Val Val Lys Thr Thr Ile Met Leu Ala Asp
 65                  70                  75                  80

Leu Ala Asp Phe Lys Thr Val Asn Glu Ile Tyr Ala Lys Tyr Phe Pro
                 85                  90                  95

Ala Pro Ser Pro Ala Arg Ser Thr Tyr Gln Val Ala Ala Leu Pro Leu
                100                 105                 110

Asn Ala Lys Ile Glu Ile Glu Cys Ile Ala Thr Leu
            115                 120

<210> SEQ ID NO 83
<211> LENGTH: 129
<212> TYPE: PRT
<213> ORGANISM: Escherichia coli

<400> SEQUENCE: 83

Met Lys Lys Ile Ile Glu Thr Gln Arg Ala Pro Gly Ala Ile Gly Pro
 1               5                  10                  15

Tyr Val Gln Gly Val Asp Leu Gly Ser Met Val Phe Thr Ser Gly Gln
             20                  25                  30

Ile Pro Val Cys Pro Gln Thr Gly Glu Ile Pro Ala Asp Val Gln Asp
             35                  40                  45

Gln Ala Arg Leu Ser Leu Glu Asn Val Lys Ala Ile Val Val Ala Ala
 50                  55                  60

Gly Leu Ser Val Gly Asp Ile Ile Lys Met Thr Val Phe Ile Thr Asp
 65                  70                  75                  80

Leu Asn Asp Phe Ala Thr Ile Asn Glu Val Tyr Lys Gln Phe Phe Asp
                 85                  90                  95
```

Glu His Gln Ala Thr Tyr Pro Thr Arg Ser Cys Val Gln Val Ala Arg
            100                 105                 110

Leu Pro Lys Asp Val Lys Leu Glu Ile Glu Ala Ile Ala Val Arg Ser
        115                 120                 125

Ala

<210> SEQ ID NO 84
<211> LENGTH: 128
<212> TYPE: PRT
<213> ORGANISM: Escherichia coli

<400> SEQUENCE: 84

Met Ser Lys Thr Ile Ala Thr Glu Asn Ala Pro Ala Ala Ile Gly Pro
1               5                   10                  15

Tyr Val Gln Gly Val Asp Leu Gly Asn Met Ile Ile Thr Ser Gly Gln
            20                  25                  30

Ile Pro Val Asn Pro Lys Thr Gly Glu Val Pro Ala Asp Val Ala Ala
        35                  40                  45

Gln Ala Arg Gln Ser Leu Asp Asn Val Lys Ala Ile Val Glu Ala Ala
    50                  55                  60

Gly Leu Lys Val Gly Asp Ile Val Lys Thr Thr Val Phe Val Lys Asp
65                  70                  75                  80

Leu Asn Asp Phe Ala Thr Val Asn Ala Thr Tyr Glu Ala Phe Phe Thr
                85                  90                  95

Glu His Asn Ala Thr Phe Pro Ala Arg Ser Cys Val Glu Val Ala Arg
            100                 105                 110

Leu Pro Lys Asp Val Lys Ile Glu Ile Glu Ala Ile Ala Val Arg Arg
        115                 120                 125

<210> SEQ ID NO 85
<211> LENGTH: 131
<212> TYPE: PRT
<213> ORGANISM: Escherichia coli

<400> SEQUENCE: 85

Met Val Glu Arg Thr Ala Val Phe Pro Ala Gly Arg His Ser Leu Tyr
1               5                   10                  15

Ala Glu His Arg Tyr Ser Ala Ala Ile Arg Ser Gly Asp Leu Leu Phe
            20                  25                  30

Val Ser Gly Gln Val Gly Ser Arg Glu Asp Gly Thr Pro Glu Pro Asp
        35                  40                  45

Phe Gln Gln Gln Val Arg Leu Ala Phe Asp Asn Leu His Ala Thr Leu
    50                  55                  60

Ala Ala Ala Gly Cys Thr Phe Asp Asp Ile Ile Asp Val Thr Ser Phe
65                  70                  75                  80

His Thr Asp Pro Glu Asn Gln Phe Glu Asp Ile Met Thr Val Lys Asn
                85                  90                  95

Glu Ile Phe Ser Ala Pro Pro Tyr Pro Asn Trp Thr Ala Val Gly Val
            100                 105                 110

Thr Trp Leu Ala Gly Phe Asp Phe Glu Ile Lys Val Ile Ala Arg Ile
        115                 120                 125

Pro Glu Gln
    130

<210> SEQ ID NO 86
<211> LENGTH: 114
<212> TYPE: PRT

<213> ORGANISM: Escherichia coli

<400> SEQUENCE: 86

Met Thr Ile Val Arg Ile Asp Ala Glu Ala Arg Trp Ser Asp Val Val
1               5                   10                  15

Ile His Asn Asn Thr Leu Tyr Tyr Thr Gly Val Pro Glu Asn Leu Asp
                20                  25                  30

Ala Asp Ala Phe Glu Gln Thr Ala Asn Thr Leu Ala Gln Ile Asp Ala
            35                  40                  45

Val Leu Glu Lys Gln Gly Ser Asn Lys Ser Ser Ile Leu Asp Ala Thr
    50                  55                  60

Ile Phe Leu Ala Asp Lys Asn Asp Phe Ala Ala Met Asn Lys Ala Trp
65                  70                  75                  80

Asp Ala Trp Val Val Ala Gly His Ala Pro Val Arg Cys Thr Val Gln
                85                  90                  95

Ala Gly Leu Met Asn Pro Lys Tyr Lys Val Glu Ile Lys Ile Val Ala
            100                 105                 110

Ala Val

<210> SEQ ID NO 87
<211> LENGTH: 128
<212> TYPE: PRT
<213> ORGANISM: Escherichia coli

<400> SEQUENCE: 87

Met Pro Lys Ser Val Ile Pro Ala Gly Ser Ser Ala Pro Leu Ala
1               5                   10                  15

Pro Phe Val Pro Gly Thr Leu Ala Asp Gly Val Val Tyr Val Ser Gly
                20                  25                  30

Thr Leu Ala Phe Asp Gln His Asn Asn Val Leu Phe Ala Asp Asp Pro
            35                  40                  45

Lys Ala Gln Thr Arg His Val Leu Glu Thr Ile Arg Lys Val Ile Glu
    50                  55                  60

Thr Ala Gly Gly Thr Met Ala Asp Val Thr Phe Asn Ser Ile Phe Ile
65                  70                  75                  80

Thr Asp Trp Lys Asn Tyr Ala Ala Ile Asn Glu Ile Tyr Ala Glu Phe
                85                  90                  95

Phe Pro Gly Asp Lys Pro Ala Arg Phe Cys Ile Gln Cys Gly Leu Val
            100                 105                 110

Lys Pro Asp Ala Leu Val Glu Ile Ala Thr Ile Ala His Ile Ala Lys
    115                 120                 125

<210> SEQ ID NO 88
<211> LENGTH: 129
<212> TYPE: PRT
<213> ORGANISM: Escherichia coli

<400> SEQUENCE: 88

Met Lys Lys Ile Ile Glu Thr Gln Arg Ala Pro Gly Ala Ile Gly Pro
1               5                   10                  15

Tyr Val Gln Gly Val Asp Leu Gly Ser Met Val Phe Thr Ser Gly Gln
                20                  25                  30

Ile Pro Val Cys Pro Gln Thr Gly Glu Ile Pro Ala Asp Val Gln Asp
            35                  40                  45

Gln Ala Arg Leu Ser Leu Glu Asn Val Lys Ala Ile Val Val Ala Ala
    50                  55                  60

```
Gly Leu Ser Val Gly Asp Ile Ile Lys Met Thr Val Phe Ile Thr Asp
65              70                  75                  80

Leu Asn Asp Phe Ala Thr Ile Asn Glu Val Tyr Lys Gln Phe Phe Asp
                85                  90                  95

Glu His Gln Ala Thr Tyr Pro Thr Arg Ser Cys Val Gln Val Ala Arg
                100                 105                 110

Leu Pro Lys Asp Val Lys Leu Glu Ile Glu Ala Ile Ala Val Arg Ser
            115                 120                 125

Ala

<210> SEQ ID NO 89
<211> LENGTH: 128
<212> TYPE: PRT
<213> ORGANISM: Escherichia coli

<400> SEQUENCE: 89

Met Ser Lys Thr Ile Ala Thr Glu Asn Ala Pro Ala Ala Ile Gly Pro
1               5                   10                  15

Tyr Val Gln Gly Val Asp Leu Gly Asn Met Ile Ile Thr Ser Gly Gln
                20                  25                  30

Ile Pro Val Asn Pro Lys Thr Gly Glu Val Pro Ala Asp Val Ala Ala
                35                  40                  45

Gln Ala Arg Gln Ser Leu Asp Asn Val Lys Ala Ile Val Glu Ala Ala
            50                  55                  60

Gly Leu Lys Val Gly Asp Ile Val Lys Thr Thr Val Phe Val Lys Asp
65              70                  75                  80

Leu Asn Asp Phe Ala Thr Val Asn Ala Thr Tyr Glu Ala Phe Phe Thr
                85                  90                  95

Glu His Asn Ala Thr Phe Pro Ala Arg Ser Cys Val Glu Val Ala Arg
                100                 105                 110

Leu Pro Lys Asp Val Lys Ile Glu Ile Glu Ala Ile Ala Val Arg Arg
            115                 120                 125
```